US009458492B2

(12) United States Patent
Iadonato et al.

(10) Patent No.: US 9,458,492 B2
(45) Date of Patent: Oct. 4, 2016

(54) METHODS AND CELLS FOR IDENTIFYING RIG-I PATHWAY REGULATORS

(75) Inventors: Shawn P Iadonato, Seattle, WA (US); Kristin Bedard, Seattle, WA (US)

(73) Assignee: Kineta, Inc., Seattle, WA (US)

( * ) Notice: Subject to any disclaimer, the term of this patent is extended or adjusted under 35 U.S.C. 154(b) by 0 days.

(21) Appl. No.: 14/001,472

(22) PCT Filed: Feb. 23, 2012

(86) PCT No.: PCT/US2012/026387
§ 371 (c)(1),
(2), (4) Date: Aug. 23, 2013

(87) PCT Pub. No.: WO2012/154271
PCT Pub. Date: Nov. 15, 2012

(65) Prior Publication Data
US 2013/0336929 A1    Dec. 19, 2013

Related U.S. Application Data

(60) Provisional application No. 61/446,898, filed on Feb. 25, 2011, provisional application No. 61/560,743, filed on Nov. 16, 2011.

(51) Int. Cl.
*C12Q 1/66* (2006.01)
*C12N 7/00* (2006.01)
*A61K 39/12* (2006.01)
*A61K 31/5415* (2006.01)
*A61K 31/353* (2006.01)
*C12Q 1/18* (2006.01)

(52) U.S. Cl.
CPC .............. *C12Q 1/66* (2013.01); *A61K 31/353* (2013.01); *A61K 31/5415* (2013.01); *C12N 7/00* (2013.01); *C12Q 1/18* (2013.01); *C12N 2760/16111* (2013.01); *C12N 2770/24111* (2013.01); *C12N 2770/24211* (2013.01)

(58) Field of Classification Search
None
See application file for complete search history.

(56) References Cited

U.S. PATENT DOCUMENTS

| 7,618,998 | B2 | 11/2009 | Tzeng et al. | |
|---|---|---|---|---|
| 7,880,059 | B2 | 2/2011 | Dixon et al. | |
| 2005/0256124 | A1 | 11/2005 | Goodfellow et al. | |
| 2007/0123566 | A1 | 5/2007 | Xu | |
| 2008/0138818 | A1 | 6/2008 | Tovey et al. | |
| 2010/0009970 | A1* | 1/2010 | Johansen et al. | 514/218 |
| 2011/0262482 | A1 | 10/2011 | Iadonato et al. | |
| 2013/0039887 | A1 | 2/2013 | Iadonato et al. | |

FOREIGN PATENT DOCUMENTS

| CN | 101301287 | | 11/2008 |
|---|---|---|---|
| CN | 101503736 | A | 8/2009 |
| JP | H0267218 | A1 | 3/1990 |
| WO | WO9949862 | A1 | 10/1999 |
| WO | WO2004111027 | A1 | 12/2004 |
| WO | WO2006002422 | A2 | 1/2006 |
| WO | WO2006034219 | A2 | 3/2006 |
| WO | WO2008080091 | A2 | 7/2008 |
| WO | WO2009018338 | A2 | 2/2009 |
| WO | WO2009052411 | A2 | 4/2009 |
| WO | WO2010032248 | A2 | 3/2010 |
| WO | WO2011133728 | A2 | 10/2011 |
| WO | 2012-003030 | | 1/2012 |
| WO | WO2012154271 | A2 | 11/2012 |
| WO | WO2015009812 | A2 | 1/2015 |

OTHER PUBLICATIONS

Iadonato (NIAID Mar. 23-24, 2011 Influenza antiviral research pipeline workshop, p. 1-43).*
Ranjith-Kumar et al. (PLoS, Sep. 2010, vol. 5, p. 1-11).*
Bedard et al. (Journal of Virology, 2012, p. 7334-7344).*
Lyu et al. (Archives in Pharm Research, 2005, p. 1293-1301).*
Banerjee, et al., "Multi-Targeted Therapy of Cancer by Genistein," Cancer Lett., 269, 226-242. (2008).
Barnard, "Animal models for the study of influenza pathogenesis and Therapy," Antiviral Res., 82, A110-122. (2009).
Blight, et al., "Highly Permissive Cell Lines for Subgenomic and Genomic Hepatitis C Virus RNA Replication," J. Virology, 76:13001-13014. (2002).
Cilloniz, et al., "Functional Genomics Reveals the Induction of Inflammatory Response and Metalloproteinase Gene Expression during Lethal Ebola Virus Infection," J. Virology, 84:7613-7624. (2010).
Daffis, et al., "Toll-Like Receptor 3 Has a Protective Role against West Nile Virus Infection," J Virol., 82, 10349-10358. (2008).
Horsmans, et al., "Isatoribine, an Agonist of TLR7, Reduces Plasma Virus Concentration in Chronic Hepatitis C Infection," Hepatology, 42, 724-731. (2005).
Johnson, et al., "CARD games between virus and host get a new player," Trends Immunol, 27, 1-4. (2006).
Kato, et al., Cell type-specific involvement of RIG-I in antiviral response, Immunity, vol. 23, No. 1, pp. 19-28. (2005).
Kato, et al., "Differential roles of MDA5 and RIG-I helicases in the recognition of RNA viruses," Nature, 441, 101-105. (2006).
Kawai, et al., "IPS-1, an adaptor triggering RIG-I- and Mda5-mediated type I interferon induction," Nat. Immunol., 6, 981-988. (2005).
Lee, et al., "Activation of anti-hepatitis C virus responses via Toll-like receptor 7," Proc. Natl. Acad. Sci. U.S.A., 103, 1828-1833. (2006).
Lescuyer, et al., "Progress in the definition of a reference human mitochondrial proteome," Proteomics, 3, 157-167. (2003).
Li, et al., "Distinct Poly(I-C) and Virus-activated Signaling Pathways Leading to Interferon-β Production in Hepatocytes," J. Biol. Chem., 280, 16739-16747. (2005).

(Continued)

Primary Examiner — Agnieszka Boesen
(74) Attorney, Agent, or Firm — Christensen O'Connor Johnson Kindness PLLC

(57) ABSTRACT

Disclosed herein are methods for identifying compounds for the treatment of viral infection, including RNA viral infection and uses of the compounds as pharmaceutical compositions. The identified compounds modulate the RIG-I pathway in vertebrate cells.

11 Claims, 21 Drawing Sheets

(56) References Cited

OTHER PUBLICATIONS

Lipinski, et al., "Experimental and computational approaches to estimate solubility and permeability in drug discovery and development settings," Adv. Drug Deliv. Rev., 46, 3-26. (2001).
Loo, et al., "Viral and therapeutic control of IFN-β promoter stimulator 1 during hepatitis C virus infection," Proc. Natl. Acad. Sci. U.S.A., 103, 6001-6006. (2006).
Loo, et al., "Distinct RIG-I and MDA5 Signaling by RNA Viruses in Innate Immunity," J. Virol., 82, 335-345. (2008).
Lutfalla, et al., "Mutant U5A cells are complemented by an interferon-αβ receptor subunit generated by alternative processing of a new member of a cytokine receptor gene cluster," EMBO J., 14, 5100-5108. (1995).
Meylan, et al., "Cardif is an adaptor protein in the RIG-I antiviral pathway and is targeted by hepatitis C virus," Nature, 437, 1167-1172. (2005).
Odaka, et al., "Ligand-Binding Enhances the Affinity of Dimerization of the Extracellular Domain of the Epidermal Growth Factor Receptor," J. Biochem., 122, 116-121. (1997).
Philo, "Dimerization of the Extracellular Domain of the Erythropoietin (EPO) Receptor by EPO: One High-Affinity and One Low-Affinity Interaction," Biochemistry, 35, 1681-1691. (1996).
Philo, et al., "Human Stem Cell Factor Dimer Forms a Complex with Two Molecules of the Extracellular Domain of Its Receptor, Kit," J. Biol. Chem., 271, 6895-6902. (1996).
Pichlmair, A. et al., "RIG-I-mediated antiviral responses to single-stranded RNA bearing 5'-phosphates", Science, vol. 314, No. 5801, pp. 997-1001. (2006).
Randall, R. E., et al., "Interferons and viruses: an interplay between induction, signalling, antiviral responses and virus countermeasures" J. Gen. Virol., vol. 89, Pt. 1, pp. 1-47. (2008).
Renard, et al., "Development of a sensitive multi-well colorimetric assay for active NFκB," Nucleic Acids Res., 29, E21. (2001).
Saito, et al., "Regulation of innate antiviral defenses through a shared repressor domain in RIG-I and LGP2," Proc. Natl. Acad. Sci. U.S.A., 104, 582-587. (2007).
Saito, et al., "Innate immunity induced by composition-dependent RIG-I recognition of hepatitis C virus RNA," Nature, 454, 523-527. (2008).
Seth, et al., "Identification and Characterization of MAVS, a Mitochondrial Antiviral Signaling Protein that Activates NFκB and IRF3," Cell, 122, 669-682. (2005).
Sumpter, et al., "Regulating Intracellular Antiviral Defense and Permissiveness to Hepatitis C Virus RNA Replication through a Cellular RNA Helicase, RIG-I," J. Virol., 79, 2689-2699. (2005).
Suthar, "IPS-1 Is Essential for the Control of West Nile Virus Infection and Immunity," PLoS Pathog, 6, e1000757. (2010).
Tan, et al., "Systems biology and the host response to viral infection," Nat. Biotechnol., 25, 1383-1389. (2007).
Taylor, et al., "Characterization of the human heart mitochondrial proteome," Nat. Biotechnol., 21, 281-286. (2003).
Venkataraman, et al., "Loss of DExD/H Box RNA Helicase LGP2 Manifests Disparate Antiviral Responses," J. Immunol., 178, 6444-6455. (2007).
Xu, et al., "VISA Is an Adapter Protein Required for Virus-Triggered IFN-β Signaling," Mol. Cell., 19, 727-740. (2005).
Yoneyama, et al., "The RNA helicase RIG-I has an essential function in double-stranded RNA-induced innate antiviral responses," Nat. Immunol., 5, 730-737. (2004).
Yoneyama, et al., "Shared and Unique Functions of the DExD/H-Box Helicases RIG-I, MDA5, and LGP2 in Antiviral Innate Immunity," J. Immunol., 175, 2851-2858. (2005).
Zou, et al., "Origin and evolution of the RIG-I like RNA helicase gene family," BMC Evol. Biol., 9, 85. (2009).
International Search Report and Written Opinion for PCT/US2012/026387.
International Preliminary Report on Patentability for PCT/US2012/026387.
STN Registration File RN 610760-41-3.
Ali, et al.,"Hepatitis C Virus Subgenomic Replicons in the Human Embryonic Kidney 293 Cell Line", J. Virol., vol. 78, No. 1, 2004, pp. 491-501.
Bedard, et al., "Small Molecule Agonists of the RIG-I Pathway and their Potent Antiviral Actions," Antiviral Research, vol. 86, No. 1, Mar. 2010, p. A25.
Bedard, et al.,"Small Molecule Agonists of the RIG-I Pathway and their Potent Immune Pathway Stimulation and Broad Antiviral Actions," Fifth Annual International Society for Vaccines, Global Congress, Seattle, WA, Oct. 3, 2011.
Cheng, et al., "Double-Stranded DNA and Double-Stranded RNA Induce a Common Antiviral Signaling Pathway in Human Cells," PNAS, vol. 104, No. 21, May 2007, pp. 9035-9040.
Dictionary.com, "Compound", Retrived on Apr. 14, 2014 at <<http://dictionary.reference. com/browsel compound>>, pp. #1-pp. #3.
Examination Report Dated Mar. 31, 2014 in European Application No. 11801290.5.
Examination Report Dated Jul. 16, 2013 in European Application No. 11772680.2.
Examination Report Dated Aug. 16, 2013 in European Application No. 11801290.5.
Evans, et al., "Claudin-1 is a Hepatitis C Virus Co-receptor Required for a Late Step in Entry," Nature, vol. 446, Apr. 2007, pp. 801-805.
Evers, et al., "Human Cytomegalovirus-Inhibitory Flavonoids: Studies on Antiviral Activity and Mechanism of Action," Antiviral Research, vol. 68, 2005, pp. 124-134.
Foy, et al., "Control of Antiviral Defenses Through Hepatitis C Virus Disruption of Retinoic Acid-Inducible Gene-I Signaling", PNAS, vol. 102, No. 8, Feb. 2005, pp. 2986-2991.
Goodchild, et al., "Primary Leukocyte Screens for Innate Immune Agonists," J. Biomol. Sciences, published online Jun. 12, 2009, pp. 1-8.
Horie, et al., 'Suppressive Effects of Traditional Herbal Medicines on Reversion of Attenuated Polio Vaccine Viruses to Neurovirulent Genotype', J. of Traditional Med., vol. 24, 2007, pp. 156-163.
Kakiuchi, et al., "A High Throughput Assay of the Hepatitis C Virus Nonstructural Protein 3 Serine Proteinase," J. Virol. Methods, vol. 80, 1999, pp. 77-84.
Kineta Press Release for "Multiple, potent, small molecules found to target RIG-I innate immune pathway" by Dr. Kristin Bedard.
Kineta Press Release for "Small Molecule Vaccine Adjuvant Compounds Activate RIG-I Innate Immune Pathway" by Dr. Myra Wang.
Lanford, et al., "Antiviral Effect and Virus-Host Interactions in Response to Alpha Interferon, Gamma Interferon, Poly(I)-Poly(C), Tumor Necrosis Factor Alpha, and Ribavirin in Hepatitis C Virus Subgenomic Replicons", J. Virol., 2003, pp. 1092-1104.
Levai, et al.,"Enantioselective Synthesis and Chiroptical Properties of Optically Active Isoflavone Expoxides", Tetrahedron, vol. 54, 1998, pp. 13105-13114.
Lin, et al., "A CRMI-dependent Nuclear Export Pathway Is Involved in the Regulation of IRF-5 Subcellular Localization," J. Bio. Chem., vol. 280, No. 4, 2005, pp. 3088-2005.
Liu, et al., "Structure-Activity Relationship of Flavonoids as Influenza Virus Neuraminidase Inhibitors and their In Vitro Anti-Viral Activities," Bioorganic & Medicinal Chem., vol. 16, 2008, pp. 7141-7147.
Liu,et al.,"Studies on the Synthesis and Antitumor Activities of Soybean Isoflavones and their Derivitives", ACTA Pharmaceutica Sinica, vol. 35, No. 8, 2000, pp. 583-586.
Lohmann, et al, "Replication of Subgenomic Hepatitis C Virus RNAs in a Hepatoma Cell Line", Science, vol. 285, No. 110, 1999, pp. 110-113.
Luke, et al., "Coexpressed RIG-I Agonist Enhances Humoral Immune Response," J. Virol., vol. 85, No. 3, Nov. 2010, pp. 1370-1383.

(56) References Cited

OTHER PUBLICATIONS

Office Action Dated Oct. 14, 2014 in Taiwan Application 100114195.
Office Action Dated Nov. 18, 2013 for Chinese Application 201180029357.7.
Office Action Dated Nov. 8, 2013 in U.S. Appl. No. 13/642,801.
Office Action Mailed Dec. 12, 2014 in U.S. Appl. No. 13/091,983.
Office Action Dated Dec. 3, 2014 in Mexican Application MX/a/2012/012354.
Final Office Action Dated Feb. 27, 2015 in U.S. Appl. No. 13/642,801.
Office Action Dated Feb. 5, 2014 in Israeli Application 222633.
Office Action Dated Feb. 7, 2014 in Australian Application 2011242689.
Office Action Dated Mar. 24, 2014 in Australian Application 2011242689.
Office Action Dated Mar. 27, 2014 in Mexican Application MX a 2012 012354.
Final Office Action Dated Apr. 14, 2014 in U.S. Appl. No. 13/642,801.
Final Office Action Dated Apr. 23, 2015 in U.S. Appl. No. 13/091,983.
Office Action Dated Aug. 10, 2014 in Israeli Application 222633.
Office Action Dated Sep. 28, 2014 for Chinese Applicaton 201180029357.7.
Office Action Dated Sep. 29, 2014 in U.S. Appl. No. 13/642,801.
Paterniti, et al., "Evidence for the Role of Peroxisome Proliferator-Activated Receptor-beta/delta in the Development of Spinal Cord Injury," J. Pharm. and Exp. Thera., vol. 333, No. 2, 2010, pp. 465-477.
Ranjith-Kumar, et al., "Agonist and Antagonist Recognition by RIG-I, a Cytoplasmic Innate Immunity Receptor", J. Bio. Chem., vol. 284, No. 2, 2009, pp. 1155-1165.
Search Report and Written Opinion Dated Dec. 30, 2014 in International Application No. PCT/US2014/046829.
Search Report and Written Opinion Dated Feb. 17, 2012 in PCT/US2011/033257.
Search Report and Written Opinion Dated Mar. 28, 2012 in PCT/US2011/033336.
Search Report Dated Dec. 5, 2014 for European Application No. 12781933.2.
Search Report Dated Aug. 16, 2013 for European Application No. 11801290.5.
STN registration file, RN 610753-87-2,2003.
Xu, et al., "Natural RNA Agonists of RIG-I Trigger a Robust Antiviral Response that Inhibits Influenza Infection," Cytokine, vol. 52, p. 60-61, 2010.
Ye, et al.,"Characterization of Anti-Coxsackie virus B3 Constituents of Radix Astragali by High-performance Liquid Chromatography Coupled with Electrospray Ionization Tandem Mass Spectrometry", Biochemical Chromatography, vol. 24, 2010, pp. 1147-1151.
Yi, et al., "Adaptive Mutations Producing Efficient Replication of Genotype 1a Hepatitis C Virus RNA in Normal Huh7 Cells," J. Virol., vol. 78, No. 15, 2004, pp. 7904-7915.
Yoneyama, et al., "Function of RIG-I-like REceptors in Antiviral Innate Immunity," J. Biological Chem., vol. 282, No. 21, p. 15315-15318, May 2007.
Yoneyama, et al., "RIG-I family RNA helicases: Cytoplasmic sensor for Antiviral Innate Immunity," Cytokine & Growth Factor Reviews, vol. 18, p. 545-551, 2007.
Examination Report Dated Mar. 24, 2015 in Australian Application No. 2011242689.
Matin, et al., "7-Hydroxy-benzopyran-4-one Derivatives: A Novel Pharmacophore of Peroxisome Proliferator-Adivated Receptor a and -y (PPARa and y) Dual Agonists", J. Med. Chem., vol. 52, 2009, pp. 6835-6850.
Office Action Dated Apr. 28, 2015 in Japanese Application No. 2013-506289.
Office Action Dated Jun. 1, 2015 in Chinese Application No. 201180029357.7.
Office Action Dated Aug. 11, 2015 in Mexican Application No. MX/a/2012/012354.
Office Action Dated Sep. 23, 2015 in U.S. Appl. No. 13/091,983.
Office Action dated Jul. 8, 2015 in Chinese Application No. 201280020298.1.
Sun Zhe et al., "The research of drug screening method based on detection of reporter genes," Chinese Pharmaceutical Journal, 2000, vol. 35, Issue 8, pp. 507-510.
Third Office Action Issued by State Intellectual Property Office mailed Mar. 25, 2016, issued in corresponding Chinese Application No. 201280020298.1, filed Feb. 23, 2012, 15 pages.

* cited by examiner

Tet:   −   +

1 – 1x10$^4$ cells; 2.5% serum
2 – 1.5x10$^4$ cells; 2.5% serum
3 – 2x10$^4$ cells; 2.5% serum
4 – 1x10$^4$ cells; 5% serum
5 – 1.5x10$^4$ cells; 5% serum
6 – 2x10$^4$ cells; 5% serum
7 – 1x10$^4$ cells; 10% serum
8 – 1.5x10$^4$ cells; 10% serum
9 – 2x10$^4$ cells; 10% serum

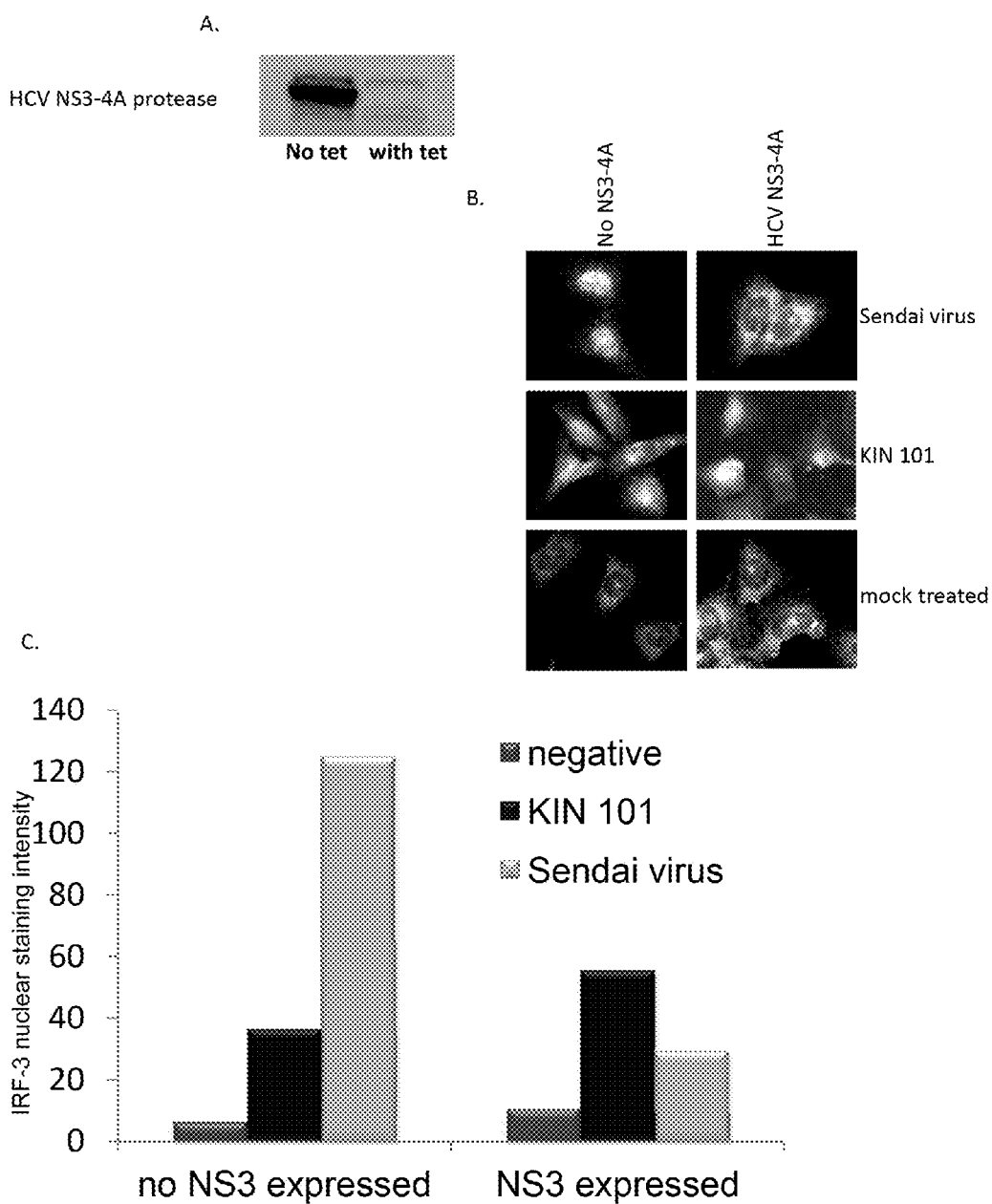

Figure 13 A/B

| Ingenuity Canonical Pathway | -log(p-value) | Genes |
|---|---|---|
| Activation of IRF by Cytosolic Pattern Recognition Receptors | 10.30 | DHX58,IFIH1,IRF7,DDX58,IRF9,STAT1,IFIT2,ISG15 |
| Interferon Signaling | 10.30 | IFIT3,IFIT1,OAS1,IFITM1,MX1,IRF9,STAT1 |
| Role of Pattern Recognition Receptors in Recognition of Bacteria and Viruses | 8.74 | IFIH1,OAS1,IRF7,OAS2,DDX58,EIF2AK2,TLR3,OAS3 |
| Role of RIG1-like Receptors in Antiviral Innate Immunity | 6.68 | DHX58,IFIH1,IRF7,DDX58,TRIM25 |
| Retinoic acid Mediated Apoptosis Signaling | 4.38 | ZC3HAV1,PARP12,PARP9,PARP14 |

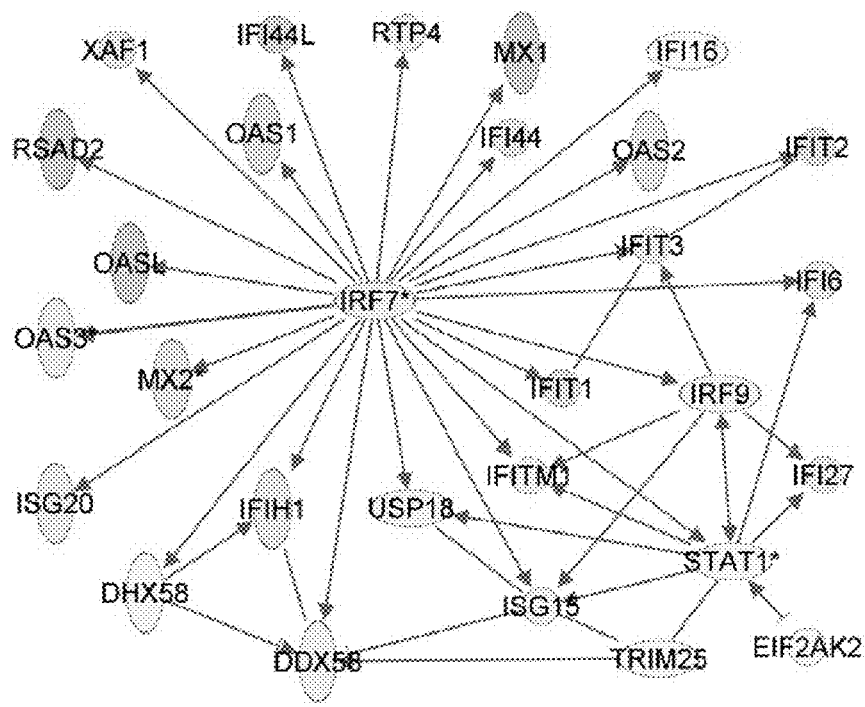

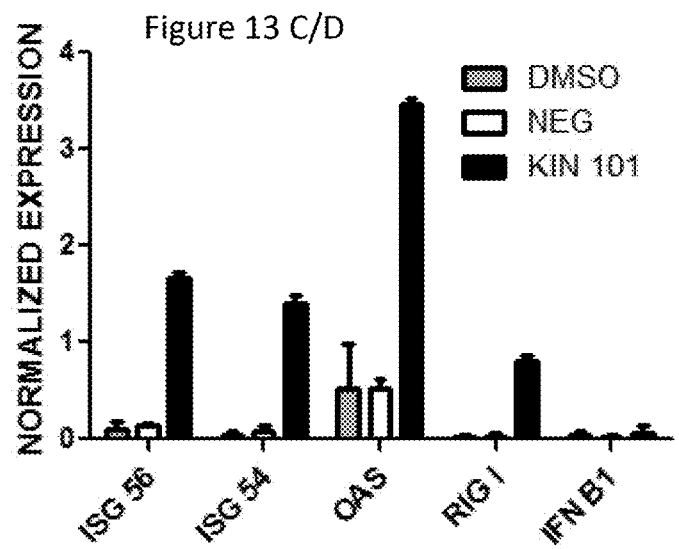
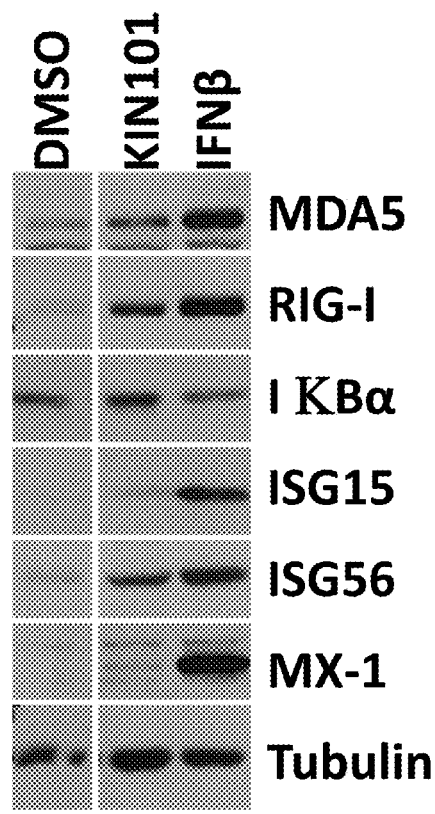

Figure 15.

| Probe ID | Gene Symbol | Negative vs. DMSO | KIN 101 vs DMSO | Sendai vs. DMSO | ANOVA P-Value* |
|---|---|---|---|---|---|
| A_23_P17663 | MX1 | 1.04 | 93.64 | 100 | 0.00203 |
| A_23_P139786 | OASL | 1.41 | 86.52 | 100 | 0.00036 |
| A_24_P28722 | RSAD2 | 1.02 | 81.78 | 100 | 0.00095 |
| A_23_P45871 | IFI44L | -1.21 | 62.62 | 100 | 0.00095 |
| A_23_P52266 | IFIT1 | 1.01 | 28.15 | 100 | 0.00036 |
| A_23_P110196 | HERC5 | -1.03 | 28.09 | 100 | 0.00203 |
| A_24_P304071 | IFIT2 | 1.50 | 26.47 | 100 | 0.00538 |
| A_23_P64828 | OAS1 | -1.01 | 26.24 | 100 | 0.00446 |
| A_23_P24004 | IFIT2 | 1.02 | 23.73 | 100 | 0.00163 |
| A_23_P250358 | HERC6 | 1.96 | 18.86 | 98.83 | 0.00203 |
| A_23_P23074 | IFI44 | 1.21 | 18.79 | 99.91 | 0.00491 |
| A_23_P250353 | HERC6 | 1.31 | 17.26 | 100 | 0.00325 |
| A_24_P343929 | OAS2 | -1.02 | 17.09 | 100 | 0.00163 |
| A_23_P6263 | MX2 | -1.56 | 15.98 | 100 | 0.00016 |
| A_23_P384355 | LOC129607 | -1.69 | 15.87 | 100 | 0.0001 |
| A_24_P20607 | CXCL11 | 1.09 | 15.72 | 100 | 0.00915 |
| A_23_P68155 | IFIH1 | 1.13 | 14.02 | 100 | 0.00446 |
| A_23_P4283 | XAF1 | 1.09 | 13.35 | 97.17 | 0.00709 |
| A_23_P35412 | IFIT3 | -1.02 | 12.33 | 100 | 0.00003 |
| A_23_P48513 | IFI27 | 1.01 | 11.45 | 100 | 0.00543 |

Figure 16

| Probe ID | Gene Symbol | Negative vs. DMSO | KIN 101 vs DMSO | Sendai vs. DMSO | ANOVA P-Value* |
|---|---|---|---|---|---|
| A_23_P17663 | MX1 | 1.04 | 93.64 | 100 | 0.00203 |
| A_23_P139786 | OASL | 1.41 | 86.52 | 100 | 0.00036 |
| A_24_P28722 | RSAD2 | 1.02 | 81.78 | 100 | 0.00095 |
| A_23_P45871 | IFI44L | -1.21 | 62.62 | 100 | 0.00095 |
| A_23_P52266 | IFIT1 | 1.01 | 28.15 | 100 | 0.00036 |
| A_23_P110196 | HERC5 | -1.03 | 28.09 | 100 | 0.00203 |
| A_24_P304071 | IFIT2 | 1.50 | 26.47 | 100 | 0.00538 |
| A_23_P64828 | OAS1 | -1.01 | 26.24 | 100 | 0.00446 |
| A_23_P24004 | IFIT2 | 1.02 | 23.73 | 100 | 0.00163 |
| A_23_P250358 | HERC6 | 1.96 | 18.86 | 98.83 | 0.00203 |
| A_23_P23074 | IFI44 | 1.21 | 18.79 | 99.91 | 0.00491 |
| A_23_P250353 | HERC6 | 1.31 | 17.26 | 100 | 0.00325 |
| A_24_P343929 | OAS2 | -1.02 | 17.09 | 100 | 0.00163 |
| A_23_P6263 | MX2 | -1.56 | 15.98 | 100 | 0.00016 |
| A_23_P384355 | LOC129607 | -1.69 | 15.87 | 100 | 0.0001 |
| A_24_P20607 | CXCL11 | 1.09 | 15.72 | 100 | 0.00915 |
| A_23_P68155 | IFIH1 | 1.13 | 14.02 | 100 | 0.00446 |
| A_23_P4283 | XAF1 | 1.09 | 13.35 | 97.17 | 0.00709 |
| A_23_P35412 | IFIT3 | -1.02 | 12.33 | 100 | 0.00003 |
| A_23_P48513 | IFI27 | 1.01 | 11.45 | 100 | 0.00543 |
| A_23_P201459 | IFI6 | -1.18809 | 10.943 | 94.38922 | 0.00709 |
| A_23_P32404 | ISG20 | 1.01918 | 9.8213 | 100 | 0.00163 |
| A_24_P117294 | MX2 | -1.60264 | 9.1843 | 85.37289 | 0.00248 |
| A_23_P4286 | XAF1 | -1.21865 | 9.06818 | 94.96381 | 0.00201 |
| A_23_P166797 | RTP4 | -1.04155 | 7.66259 | 100 | 0.00121 |
| A_23_P47955 | OAS3 | 1.0392 | 7.21917 | 81.74078 | 0.00373 |
| A_24_P334361 | DDX60 | 1.17962 | 6.11489 | 42.15301 | 0.0042 |
| A_23_P69383 | PARP9 | -1.0182 | 5.8888 | 18.26447 | 0.00062 |

Figure 16 (Cont.)

| | | | | |
|---|---|---|---|---|
| A_23_P72737 | IFITM1 | -1.02828 | 57.37966 | 0.00972 |
| A_23_P41470 | DDX60 | 1.08043 | 38.51897 | 0.00709 |
| A_23_P20814 | DDX58 | -1.03221 | 36.56878 | 0.00325 |
| A_24_P378019 | IRF7 | 1.02821 | 21.08394 | 0.00055 |
| A_23_P39465 | BST2 | -1.06155 | 100 | 0.00501 |
| A_23_P69109 | PLSCR1 | 1.08655 | 16.16749 | 0.00976 |
| A_24_P335305 | OAS3 | -1.08266 | 54.83585 | 0.00446 |
| A_23_P370682 | BATF2 | -1.06042 | 59.80706 | 0.00062 |
| A_24_P175187 | SAMD9 | 1.31767 | 16.94687 | 0.00446 |
| A_23_P819 | ISG15 | -1.01367 | 40.58691 | 0.00042 |
| A_24_P927166 | AF085913 | 1.06397 | 30.44048 | 0.00248 |
| A_24_P175188 | SAMD9 | 1.00629 | 16.71001 | 0.0094 |
| A_23_P20122 | ZC3HAV1 | 1.18511 | 30.49334 | 0.00252 |
| A_23_P111804 | PARP12 | 1.0041 | 10.70685 | 0.00121 |
| A_23_P75786 | SLC15A3 | 1.09558 | 37.53519 | 0.0068 |
| A_32_P132206 | USP18 | 1.04874 | 20.19221 | 0.00095 |
| A_24_P118892 | IRF7 | 1.14298 | 15.11711 | 0.00808 |
| A_24_P941912 | DTX3L | 1.19669 | 8.54045 | 0.00095 |
| A_23_P132159 | USP18 | 1.04495 | 20.13898 | 0.00163 |
| A_24_P161018 | PARP14 | 1.06416 | 18.20648 | 0.00394 |
| A_32_P99533 | ISG15 | 1.04402 | 8.5963 | 0.00188 |
| A_23_P65442 | IRF9 | 1.00643 | 5.79734 | 0.00095 |
| A_23_P104798 | IL18 | 1.23842 | 1.63268 | 0.00095 |
| A_23_P355244 | SAMD9 | -1.00306 | 17.51886 | 0.00424 |
| A_23_P161218 | ANKRD1 | 1.14079 | 2.49979 | 0.00429 |
| A_23_P145874 | SAMD9L | 1.05772 | 18.71014 | 0.00602 |
| A_23_P215060 | PODXL | 1.00188 | 7.08806 | 0.00203 |
| A_23_P347040 | DTX3L | 1.11076 | 8.42229 | 0.00497 |
| A_32_P54553 | USP41 | -1.08783 | 18.2251 | 0.00864 |
| A_23_P29922 | TLR3 | 1.08334 | 51.69365 | 0.00951 |
| A_23_P216655 | TRIM14 | 1.02698 | 6.21023 | 0.00095 |

Figure 16 (Cont.)

| Probe | Gene | Value1 | Value2 | Value3 |
|---|---|---|---|---|
| A_23_P433855 | RGS4 | 1.16682 | 2.88325 | -1.36225 | 0.00203 |
| A_23_P38346 | DHX58 | 1.0494 | 2.85988 | 39.39326 | 0.00694 |
| A_23_P30069 | DDX60L | -1.01195 | 2.82383 | 12.34878 | 0.00324 |
| A_23_P138194 | NCF2 | -1.0981 | 2.62988 | 11.20346 | 0.0084 |
| A_23_P46618 | PLXNA2 | 1.03147 | 2.61808 | 2.25979 | 0.00394 |
| A_24_P274270 | STAT1 | -1.04935 | 2.52406 | 10.868 | 0.00468 |
| A_24_P158089 | SERPINE1 | 1.02135 | 2.35573 | 1.50773 | 0.00181 |
| A_32_P38003 | ENST00000379156 | -1.00742 | 2.33916 | 3.05628 | 0.00446 |
| A_23_P200737 | RGS4 | 1.06303 | 2.32854 | -1.35394 | 0.00203 |
| A_24_P262127 | RRAD | 1.16359 | 2.30976 | 42.04013 | 0.00967 |
| A_23_P56630 | STAT1 | -1.0061 | 2.28217 | 7.35432 | 0.00416 |
| A_23_P217866 | IFI16 | 1.07825 | 2.22385 | 4.37741 | 0.00845 |
| A_24_P23034 | ZNFX1 | 1.0603 | 2.18998 | 5.27258 | 0.00424 |
| A_23_P47691 | TRIM21 | -1.12961 | 2.16174 | 4.72837 | 0.00891 |
| A_23_P873 | C1orf38 | 1.01945 | 2.14189 | 10.22331 | 0.00422 |
| A_24_P936767 | TRIM25 | 1.04169 | 2.12891 | 3.01075 | 0.00446 |
| A_23_P124190 | TRIM34 | 1.14575 | 2.06396 | 3.0059 | 0.00882 |
| A_24_P140608 | HBEGF | -1.06966 | 2.01585 | 1.34469 | 0.00203 |
| A_23_P154488 | PNPT1 | 1.09566 | 2.01184 | 4.20704 | 0.00325 |
| A_23_P118254 | FOXF1 | 1.08376 | -2.06676 | -1.45471 | 0.00713 |
| A_23_P329822 | GREM2 | 1.11864 | -2.27798 | -1.3813 | 0.00203 |
| A_23_P97181 | GREM2 | -1.06664 | -2.35514 | -2.1331 | 0.00788 |
| A_24_P672240 | ENST00000380682 | 1.01696 | -2.41325 | 1.05464 | 0.00325 |
| A_24_P911678 | PDE5A | -1.11813 | -2.67207 | -3.43781 | 0.00764 |
| A_23_P121987 | TSLP | 1.09128 | -2.72645 | 1.97441 | 0.00808 |
| A_23_P71530 | TNFRSF11B | -1.13508 | -2.90112 | -1.9542 | 0.0094 |
| A_32_P101917 | LOC283904 | 1.00944 | -2.9506 | -1.6201 | 0.00446 |
| A_32_P165477 | SLC7A11 | 1.04667 | -3.27946 | -2.62231 | 0.00062 |
| A_32_P96085 | A_32_P96085 | -3.67322 | -3.32334 | -1.98646 | 0.00312 |
| A_23_P360079 | NAP5 | 1.04167 | -3.97599 | -1.13809 | 0.00504 |
| A_24_P1949 | NPTX1 | 1.00451 | -18.68381 | 1.86833 | 0.00095 |

SEQUENCE LISTING

<160> NUMBER OF SEQ ID NOS: 11

<210> SEQ ID NO 1
<211> LENGTH: 2068
<212> TYPE: DNA
<213> ORGANISM: Hepatitis C virus

<400> SEQUENCE: 1

```
atacctccaa ggggtggagt cttctcgccc ccatcacagc ttacgctcag caaacacggg      60
gtcttttggg cactatagtg gtgagtatga cggggcgcga caagacggaa caggccgggg     120
aaatccaggt cctgtccacg gtcactcagt ccttcctcgg aacatccata tcgggggttt     180
tatggaccgt ctaccatgga gctggcaaca agaccctagc cggctcacgg ggcccggtca     240
cgcagatgta ttccagcgct gagggggact tggtaggatg gcccagccct cccgggacta     300
agtccttgga gccgtgcacg tgtggagcgg tcgacctgta cctggtcacg cggaacgctg     360
acgtcatccc ggctcgaaga cgcggggaca agcggggagc gctactctcc ccgagacccc     420
tttcgacctt gaagggtcc tcgggggac cggtgctttg ccccaggggc cacgctgtcg     480
ggatcttccg ggcagctgtg tgctctcggg gcgtggctaa gtccatagat ttcatccccg     540
tcgaggcgct tgacatcgtc acgcggtccc ccaccttcag tgataacagc acgccacctg     600
ctgtgcccca gacctaccag gtcgggtact tacatgctcc aactggcagt ggaaagagca     660
ccaaagtccc tgtcgcatac gcctcccagg ggtataaagt gctagtgctt aatccctcgg     720
tggctgccac cctggggttt ggggcatacc tgtctaaggc acatggcatc aatcccaaca     780
ttaggactgg ggtcaggact gtgacgaccg gagaacccat cacgtactcc acatatggta     840
aattcctcgc cgatggggc tgcacaggcg gcgcctacga catcatcata tgcgatgaat     900
gccattccat ggatgccacc accatcctcg gcatcggaac agtccttgat caagcagaga     960
cagccggggt caggttaact gtgctggcta cggccacgcc ccctgggtcg gtgacaaccc    1020
cccaccccaa tatagaggag gtagccctcg ggcaggaggg tgagatcccc ttctatggga    1080
gggcgattcc cctatcttac atcaagggg ggagacactt gatcttctgc cattcaaaga    1140
```

```
agaagtgcga cgagctcgcg gcggcccttc ggggcatggg cttgaacgca gtggcatatt   1200
acagagggct ggacgtctcc ataattccaa ctcagggaga tgtggtggtc gtcgccaccg   1260
acgccctcat gacggggtac actggggact ttgactccgt gatcgactgt aacgtagcgg   1320
tcactcaagt tgtagacttc agcctggacc ccaccttcac tataaccaca cagactgtcc   1380
ctcaggacgc cgtctcgcgt agccagcgcc gggggcgcac gggtagggga cgattgggca   1440
tttataggta tgtttctact ggtgagcgag cctcaggaat gtttgatagt gtagtgctct   1500
gtgagtgcta cgacgcgggg gccgcgtggt atgagctcac accagcagag accaccgtca   1560
ggctcagagc gtatttcaac acacccggcc tgcctgtgtg ccaggaccat cttgagtttt   1620
gggaggcagt tttcaccggc ctcacacaca tagatgccca cttcctttcc caaacaaagc   1680
aagcagggga caatttcgcg tacctaacag cctatcaggc tacggtgtgc gccagagcca   1740
aagcccctcc cccgtcctgg gacgtcatgt ggaagtgctt gactcgactc aagcccacgc   1800
tcgtgggccc cacgcctctc ctataccgct taggcactgt taccaatgag atcaccctca   1860
cacatcctgt gacgaaatac atcgccactt gcatgcaagc cgaccttgag atcatgacca   1920
gcacgtgggt cttggctggg ggagtcttgg cggctgtcgc tgcgtactgc ctggcaaccg   1980
ggtgtgtttc catcatcggc cgcttgcaca tcaatcagcg agctgtcgtc gcaccggaca   2040
aggaggtcct ctatgaggct ttcgatga                                      2068
```

```
<210> SEQ ID NO 2
<211> LENGTH: 2025
<212> TYPE: DNA
<213> ORGANISM: GBV-B virus

<400> SEQUENCE: 2
```

```
gcacctttta cgctgcagtg tctctctgaa cgtggcacgc tgtcagcgat ggcagtggtc     60
atgactggta tagacccccg aacttggact ggaactatct tcagattagg atctctggcc    120
actagctaca tgggatttgt ttgtgacaac gtgttgtata ctgctcacca tggcagcaag    180
gggcgccggt tggctcatcc cacaggctct atacacccaa taaccgttga cgcggctaat    240
gaccaggaca tctatcaacc accatgtgga gctgggtccc ttactcggtg ctcttgcggg    300
gagaccaagg ggtatctggt aacacgactg gggtcattgg ttgaggtcaa caaatccgat    360
gacccttatt ggtgtgtgtg cggggccctt cccatggctg ttgccaaggg ttcttcaggt    420
gccccgattc tgtgctcctc cgggcatgtt attgggatgt tcaccgctgc tagaaattct    480
ggcggttcag tcagtcagat tagggttagg ccgttggtgt gtgctggata ccatccccag    540
tacacagcac atgccactct tgatacaaaa cctactgtgc ctaacgagta ttcagtgcaa    600
attttaattg cccccactgg cagcggcaag tcaaccaaat taccactttc ttacatgcag    660
gagaagtatg aggtcttggt cctaaatccc agtgtggcta caacagcatc aatgccaaag    720
tacatgcacg cgacgtacgg cgtgaatcca aattgctatt ttaatggcaa atgtaccaac    780
acaggggctt cacttacgta cagcacatat ggcatgtacc tgaccggagc atgttcccgg    840
aactatgatg taatcatttg tgacgaatgc catgctaccg atgcaaccac cgtgttgggc    900
attggaaagg tcctaaccga agctccatcc aaaaatgtta ggctagtggt tcttgccacg    960
gctacccccc ctggagtaat ccctacacca catgccaaca taactgagat tcaattaacc   1020
gatgaaggca ctatcccctt tcatggaaaa aagattaagg aggaaaatct gaagaaaggg   1080
agacacctta tctttgaggc taccaaaaaa cactgtgatg agcttgctaa cgagttagct   1140
```

| | | |
|---|---|---|
| cgaaagggaa taacagctgt ctcttactat agggggatgtg acatctcaaa aatccctgag | 1200 | |
| ggcgactgtg tagtagttgc cactgatgcc ttgtgtacag ggtacactgg tgactttgat | 1260 | |
| tccgtgtatg actgcagcct catggtagaa ggcacatgcc atgttgacct tgaccctact | 1320 | |
| ttcaccatgg gtgttcgtgt gtgcggggtt tcagcaatag ttaaaggcca gcgtaggggc | 1380 | |
| cgcacaggcc gtgggagagc tggcatatac tactatgtag acgggagttg taccccttcg | 1440 | |
| ggtatggttc ctgaatgcaa cattgttgaa gccttcgacg cagccaaggc atggtatggt | 1500 | |
| ttgtcatcaa cagaagctca aactattctg gacacctatc gcacccaacc tgggttacct | 1560 | |
| gcgataggag caaatttgga cgagtgggct gatctctttt ctatggtcaa ccccgaacct | 1620 | |
| tcatttgtca atactgcaaa agaactgct gacaattatg ttttgttgac tgcagcccaa | 1680 | |
| ctacaactgt gtcatcagta tggctatgct gctcccaatg acgcaccacg gtggcaggga | 1740 | |
| gccccggcttg ggaaaaaacc ttgtgggggtt ctgtggcgct tggacggcgc tgacgcctgt | 1800 | |
| cctggcccag agcccagcga ggtgaccaga taccaaatgt gcttcactga agtcaatact | 1860 | |
| tctgggacag ccgcactcgc tgttggcgtt ggagtggcta tggcttatct agccattgac | 1920 | |
| acttttggcg ccacttgtgt gcggcgttgc tggtctatta catcagtccc taccggtgct | 1980 | |
| actgtcgccc cagtggttga cgaagaagaa atcgtggagg agtgt | 2025 | |

<210> SEQ ID NO 3
<211> LENGTH: 2415
<212> TYPE: DNA
<213> ORGANISM: Hepatitis A virus

<400> SEQUENCE: 3

| | | |
|---|---|---|
| ggaatttcag atgatgataa tgatagtgca gtagctgagt ttttccagtc ttttccatct | 60 | |
| ggtgaaccat cgaactctaa attatctggc ttttttccaat ctgttactaa tcacaagtgg | 120 | |
| gttgctgtgg gagctgcagt tggcattctt ggagtgctcg ttggaggatg gtttgtgtat | 180 | |
| aagcatttct cccgcaaaga ggaggaacca atcccagctg aaggggtata tcatggtgta | 240 | |
| actaagccca agcaagtgat taaattagat gcagatccag tagaatctca gtcaactttg | 300 | |
| gaaatagcag gactggttag gaagaacttg gttcagtttg gagttggaga agaatgga | 360 | |
| tgtgtgagat gggttatgaa tgccttggga gtgaaagatg attggctgct tgtgccttcc | 420 | |
| catgcttata aatttgagaa agattatgaa atgatggagt tttatttaa tagaggtgga | 480 | |
| acttactatt caatttcagc tggtaatgtt gttattcaat ctttggatgt gggattccag | 540 | |
| gatgttgttc tgatgaaggt tcctacaatt cctaagttta gagatattac tcagcatttt | 600 | |
| attaagaaag gggatgtgcc tagagctttg aatcgcctgg caacattagt gacaactgta | 660 | |
| aatggaaccc ctatgttaat ttctgagggc ccactaaaga tggaagagaa agctactat | 720 | |
| gttcataaga aaaatgatgg tacaacagtt gatttaactg tggatcaggc atggagagga | 780 | |
| aaaggcgaag tcttcctgg aatgtgtggt gggggccttgg tttcatcgaa tcaatctata | 840 | |
| cagaatgcaa tcttgggcat ccatgttgct ggaggaaatt caattcttgt tgcaaaattg | 900 | |
| gttactcaag aaatgttcca aaatattgat aagaaattg aaagtcagag aattatgaaa | 960 | |
| gtggagttta ctcagtgttc aatgaatgtg gtctccaaaa cgcttttag aaagagtccc | 1020 | |
| attatcatc acattgataa aaccatgatt aattttcctg cagctatgcc ttttctaaa | 1080 | |
| gctgaaattg atccaatggc tgtgatgtta tctaagtatt cattacctat tgtagaagaa | 1140 | |
| ccagaggatt ataagagggc ttcaattttt tatcaaaata aaatagtggg taagactcag | 1200 | |
| ttagttgatg atttttaga tcttgatatg gccattacag gggcccagg aattgatgct | 1260 | |

```
atcaacatgg attcatctcc tggatttcct tatgtccagg agaagttgac caaaagagat    1320
ttaatttggt tggatgaaaa tggtttattg ctgggagttc atccaagatt ggctcagaga    1380
atcttattca atactgtcat gatggaaaat tgttctgatt tggatgttgt ttttacaacc    1440
tgtccaaaag atgaattgag accattagag aaagtgttgg aatcaaaaac aagagctatt    1500
gatgcttgtc ctctggatta ctcaattttg tgccgaatgt attggggtcc agctattagt    1560 tatttttcatt tgaatccagg tttccataca ggtgttgcta ttggcataga tcctgataga    1620
cagtgggatg aattatttaa acaatgata agattcggag atgttggtct tgatttagat    1680
ttctctgctt tgatgctag tcttagtcca tttatgatta gagaagcagg tagaatcatg    1740
agtgaactat ctggaactcc atcccatttt ggcacagctc ttatcaatac tatcatttat    1800
tccaagcatt tgctgtataa ctgttgttac catgtctgtg gttcaatgcc ctctgggtct    1860
ccttgtacag ctttgctaaa ttcaattatt aataatgtca atttgtatta tgtgttttcc    1920
aagatatttg gaaagtctcc agttttcttt tgtcaggctt tgaagattct ctgttatgga    1980
gatgatgttt taatagtttt ctctcgagat gttcagattg ataatcttga tttgattgga    2040
caaaaaattg tagatgagtt taagaaactt ggcatgacag ctacttctgc tgacaagaat    2100
gtacctcagc tgaaaccagt ttcggaattg acttttctca aaagatcttt caatttggta    2160
gaggatagaa ttagacctgc aatttcggaa aaacaattt ggtctttaat agcatggcag    2220
agaagtaacg ctgagtttga gcagaattta gaaaatgctc agtggtttgc ttttatgcat    2280
ggctatgagt tttatcagaa attttattat tttgttcagt cctgtttgga gaaagagatg    2340
atagaataca gacttaaatc ttatgattgg tggagaatga gatttatga ccagtgtttc    2400 atttgtgacc tttca                                                    2415
```

<210> SEQ ID NO 4
<211> LENGTH: 848
<212> TYPE: DNA
<213> ORGANISM: Paramyxovirus

<400> SEQUENCE: 4
atgaataaca ccgagatcat tgagaatgcc tctaaagttt tggaagcgat tgatgccgcc 60
aaagaagaag agctcagaaa ccttaactct cttgtccaac caagagcccc tctcaatgca 120
ggatccaccc ctggtgagat catcaacgag atcaagcatc tatccacccg tgatcaagaa 180
gggggaacat cgagcaaaga cgaagaggaa tcaggagctg gcagaacagt tgctgaagga 240
gctgccacac gagaccacaa gtatagcaaa tctcgtccaa agaaacaacc gagatctgga 300
ttacaatctg gagcagctgg taagaaccct actccagatg gagaaggagg ggacacatgt 360
aacagagagc ttgatcaaca ctctgatgga gacggacact ctaacaccga aggagcaagc 420
tctgatctgg ccagcataca accttgtcag acagatgatg caccatgcag ctctacatca 480
tatttagatg aagaagatga accagctgta aggccaaaaa cccagtgcaa gcaatctggg 540
ttaattgagt cgaaggaaga tgaagatgga atgctttctg aactccatga acagcacaaa 600
ggccgttcta agcgactatc ggcattggga agggtgaatt cctcaccaat tccatctcca 660
agacctgacg aattgcttaa aaaaggcatc ggagagagta tagtatggtc tggtcgaatg 720
acggagtctt tattgagtca tggtgtaatc caatgtgtgc caggatcaga ccgttaccaa 780
tccgggaaat ctgtgtctgt ggccgatgcc cacttaaatg ctcgaagtgc ctgctggacc 840
cagaataa 848

<210> SEQ ID NO 5
<211> LENGTH: 890
<212> TYPE: DNA
<213> ORGANISM: Influenza virus

<400> SEQUENCE: 5

```
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aaggggcagc actcttggtc     180
tggacatcga gacagccaca cgtgctggaa agcagatagt ggagcggatt ctgaaagaag     240
aatccgatga ggcacttaaa atgaccatgg cctctgtacc tgcgtcgcgt tacctaaccg     300
acatgactct tgaggaaatg tcaagggaat ggtccatgct catacccaag cagaaagtgg     360
caggccctct ttgtatcaga atggaccagg cgatcatgga taaaaacatc atactgaaag     420
cgaacttcag tgtgattttt gaccggctgg agactctaat attgctaagg gctttcaccg     480
aagagggagc aattgttggc gaaatttcac cattgccttc tcttccagga catactgctg     540
aggatgtcaa aaatgcagtt ggagtcctca tcggaggact tgaatggaat gataacacag     600
ttcgagtctc tgaaactcta cagagattcg cttggagaag cagtaatgag aatgggagac     660
ctccactcac tccaaaacag aaacgagaaa tggcgggaac aattaggtca gaagtttgaa     720
gaaataagat ggttgattga agaagtgaga cacaaactga aggtaacaga aatagttttt     780
gagcaaataa catttatgca agccttacat ctattgcttg aagtggagca agagataaga     840
actttctcat tcagcttat ttaataataa aaaacaccct tgtttctact                 890
```

<210> SEQ ID NO 6
<211> LENGTH: 1405
<212> TYPE: DNA
<213> ORGANISM: Ebola virus

<400> SEQUENCE: 6

```
aaaaacattt gatgaagatt aaaaccttca tcgccagtaa atgattatat tgtctgtagg      60
caggtgttta ctccacctta aatttggaaa tatcctacct taggaccatt gtcaagaggt     120
gcataggcat taccacccct gagaacatgt acaataataa attgaaggta tgttcaggcc     180
cagaaacgac tggatggatt tctgagcaac ttatgacagg taagattcca gtaactgata     240
tattcattga tattgataac aagccagatc aaatggaagt ccgactcaaa ccatcatcaa     300
ggagctcaac aagaacttgt acaagtagca gtcagacgga ggtcaactat gtacctctcc     360
ttaaaaaggt tgaggataca ttaactatgc tagtgaatgc caccagtcgt cagaatgctg     420
caatcgaggc ccttgaaaac cgcctcagca cacttgagag tagcttaaag ccaatccaag     480
acatgggtaa agtgatttca tcattgaatc gcagttgtgc cgaaatggtt gcaaaatatg     540
atcttctagt tatgacaact ggacgggcta cttcaactgc agctgcagta gatgcgtatt     600
ggaaagagca caaacagcca ccaccagggc cagcgttgta tgaagagaat gcgcttaaag     660
gaaaaatcga tgatccaaac agctatgtac cagatgctgt gcaagaggct acaagaacc      720
ttgacagtac atcgacctg accgaggaaa ttttgggaa accttatata tctgctaaag     780
acctgaagga gatcatgtat gatcatctac ctggtttgg gactgccttt caccaacttg     840
ttcaagtgat tgtaaaaata ggaaaggata caacccttt ggacacaatc catgctgagt     900
tccaggcaag tctagcagat ggtgactctc cccaatgtgc actcatacag ataaccaaaa     960
gggtcccaat ctttcaggat gtgccgcccc cgataatcca tattagatcc cgtggtgaca    1020
```

```
tcccacgagc atgccaaaag agtctccgac cagcaccacc atcacccaaa attgatcgtg    1080
gttgggtttg tttgtttaag atgcaagatg gtaaaacgct tggacttaag atctaagaat    1140
caagatttat ttaacaaggc aagccacaac cttagatgga acctcagcca gactattgaa    1200
ctattgacgc tgttgatgat aatatataat taatggtctt atttgaatat gacaacatct    1260
tgcttcttgt tctgccttgt agctctttga attggaagat cattccaaac ttacaaacat    1320
gcacaagatg ttatggttta gcaaagaatt gataggagta ctggtatata atgtaaatat    1380
aacaagtgat gaagattaag aaaaa                                          1405

<210> SEQ ID NO 7
<211> LENGTH: 532
<212> TYPE: DNA
<213> ORGANISM: respiratory syncytial virus

<400> SEQUENCE: 7
ggggcaaata agaatttgat aagtaccact taaatttaac tcccttggtt agagatgggc      60
agcaattcat tgagtatgat aaaagttaga ttacaaaatt tgtttgacaa tgatgaagta    120
gcattgttaa aaataacatg ctatactgac aaattaatac atttaactaa tgcattggct    180
aaggcagtga tacatacaat caaattgaat ggcattgtat ttgtgcatgt tattacaagt    240
agtgatattt gccctaataa taatattgta gtgaaatcca atttcacaac aatgccagtg    300
ttacaaaatg gaggttatat atgggaaatg atggaattaa cacactgctc tcaacctaat    360
ggcctaatag atgacaattg tgaaattaaa ttctccaaaa aactaagtga ttcaacaatg    420
accaattata tgaatcaatt atctgaatta cttggatttg atcttaatcc ataaattata    480
ataaatatca actagcaaat caatgtcact aacaccatta gttaatataa aa            532

<210> SEQ ID NO 8
<211> LENGTH: 502
<212> TYPE: DNA
<213> ORGANISM: respiratory syncytial virus

<400> SEQUENCE: 8
ggggcaaata aatcaattca gccgacccaa ccatggacac aacacacaat gacaccacac      60
cacaaagact gatgatcaca gacatgagac cattgtcact tgagactata ataatatcac    120
taaccagaga catcataaca cacagattta tacttgataa aatcatgaa tgtatagtga     180 gaaaacttga tgaaagacag gccacattta cattcctggt caactatgaa atgaaactat    240
tgcacaaagt gggaagcact aaatacaaaa atatactga atacaacaca aaatatggca    300
cttttcctat gccaatattt atcaatcatg atgggttctt agaatgcatt ggcattaagc    360
ctacaaagca cactcccata atatacaagt atgatctcaa tccatgaatt tcaacacaag    420
agtcacacaa tctgaaataa caacttcatg cataaccaca ctccatagtt caaatggagc    480
ctgaaaatta tagtaatta aa                                              502

<210> SEQ ID NO 9
<211> LENGTH: 23
<212> TYPE: DNA
<213> ORGANISM: Homo sapiens

<400> SEQUENCE: 9
gggagctccc caaggcggcc aac                                             23

<210> SEQ ID NO 10
```

```
<211> LENGTH: 23
<212> TYPE: DNA
<213> ORGANISM: Homo sapiens

<400> SEQUENCE: 10
ggaagcttgg tctcggcggt ggt                                              23

<210> SEQ ID NO 11
<211> LENGTH: 132
<212> TYPE: DNA
<213> ORGANISM: Homo sapiens

<400> SEQUENCE: 11
ctaaaatgta aatgacatag gaaaactgaa agggagaagt gaaagtggga aattcctctg      60
aatagagaga ggaccatctc atataaatag gccataccca tggagaaagg acattctaac    120
tgcaaccttt cg                                                        132
```

US 9,458,492 B2

METHODS AND CELLS FOR IDENTIFYING RIG-I PATHWAY REGULATORS

CROSS REFERENCE TO RELATED APPLICATIONS

This application is a national phase of International Patent Application No. PCT/US2012/026387, filed on Feb. 23, 2012, which claims the benefit of U.S. Provisional Application No. 61/446,898 filed on Feb. 25, 2011 and U.S. Provisional Application No. 61/560,743 filed on Nov. 16, 2011, each of which is incorporated herein by reference in their entirety.

STATEMENT OF GOVERNMENT INTEREST

This invention was made with government support under National Institutes of Health Grant No. AI081335. The government has certain rights in the invention.

FIELD OF THE DISCLOSURE

Methods disclosed herein are useful for identifying compounds for treating viral infection in vertebrates, including RNA viral infections. The identified compounds modulate the RIG-I pathway.

BACKGROUND OF THE DISCLOSURE

As a group, RNA viruses represent an enormous public health problem in the U.S. and worldwide. Well-known RNA viruses include influenza virus (including the avian and swine isolates), hepatitis C virus (HCV), West Nile virus, SARS-coronavirus, respiratory syncytial virus (RSV), and human immunodeficiency virus (HIV).

More than 170 million people worldwide are infected by HCV, and 130 million of those are chronic carriers at risk of developing chronic liver diseases (cirrhosis, carcinoma, and liver failure). As such, HCV is responsible for two thirds of all liver transplants in the developed world. Recent studies show that the death rate from HCV infection is rising due to the increasing age of chronically infected patients. Likewise seasonal flu infects 5-20% of the population resulting in 200,000 hospitalizations and 36,000 deaths each year.

Compared to influenza and HCV, West Nile virus causes the lowest number of infections, 663 in the United States in 2009. Twenty percent of infected patients develop a severe form of the disease, resulting in a 4.5% mortality rate. Unlike influenza and HCV, there are no approved therapies for the treatment of West Nile virus infection, and it is a high-priority pathogen for drug development due to its potential as a bioterrorist agent.

Among the RNA viruses listed, vaccines exist only for influenza virus. Accordingly, drug therapy is essential to mitigate the significant morbidity and mortality associated with these viruses. Unfortunately, the number of antiviral drugs is limited, many are poorly effective, and nearly all are plagued by the rapid evolution of viral resistance and a limited spectrum of action. Moreover, treatments for acute influenza and HCV infections are only moderately effective. The standard of care for HCV infection, PEGylated interferon and ribavirin, is effective in only 50% of patients, and there are a number of dose-limiting side effects associated with the combined therapy. Both classes of acute influenza antivirals, adamantanes and neuraminidase inhibitors, are only effective within the first 48 hours after infection, thereby limiting the window of opportunity for treatment. High resistance to adamantanes already restricts their use, and massive stockpiling of neuraminidase inhibitors will eventually lead to overuse and the emergence of resistant strains of influenza.

Most drug development efforts against these viruses target viral proteins. This is a large part of the reason that current drugs are narrow in spectrum and subject to the emergence of viral resistance. Most RNA viruses have small genomes and many encode less than a dozen proteins. Viral targets are therefore limited. Based on the foregoing, there is an immense and unmet need for effective treatments against viral infections.

SUMMARY OF THE DISCLOSURE

Methods disclosed herein incorporate the fact that viral countermeasures cause a down-regulation of pathways that are essential for viral clearance. One such pathway is the RIG-I pathway. Methods disclosed herein provide means to identify compounds that can reverse or reduce the down-regulation of such pathways in the presence of viral countermeasures and provide effective strategies for new antiviral drug development.

As a non-limiting example, HCV viral machinery contributes to resistance to antiviral therapeutics and chronic host infection. The HCV NS3/4A protease inhibits the innate immune response by abrogation of the RIG-I receptor dependent signaling pathway. Therefore, methods disclosed herein identify modulators of this pathway that act downstream of or circumvent the NS3/4A interference point. These modulators represent possible therapeutic agents that can contribute to more efficient treatments of HCV infection. Accordingly, the methods disclosed herein are designed to identify modulators that have activity in the presence of antiviral interference. These approaches can be applied to many viral systems. In one embodiment, the modulators are agonists.

The present disclosure helps to meet the need for effective virus treatment methods by providing methods to identify structural classes of compounds that modulate innate immune signaling in the presence of viral countermeasures. The identified structural classes of compounds shift the focus of viral drug development away from the targeting of viral proteins to the development of drugs that target and modulate the host's innate antiviral response. Such compounds and methods are likely to be more effective, less susceptible to the emergence of viral resistance, cause fewer side effects and be effective against a range of different viruses (1). In one embodiment the compounds stimulate and/or enhance innate immune signaling.

As stated, the RIG-I pathway is intimately involved in regulating the innate immune response to RNA virus infections. RIG-I modulators are expected to be useful for the treatment of many viruses including, without limitation, HCV, influenza, and West Nile virus. Accordingly, the present disclosure relates to methods to identify compounds for treating viral infection, including infection by RNA viruses, wherein the compounds modulate, and in a particular embodiment, stimulate and/or enhance, RIG-I pathway signaling.

The disclosure provides methods of identifying compounds that modulate the activity of RIG-I, comprising the steps of: providing cells comprising a luciferase reporter gene under the control of a promoter; contacting the cells with putative RIG-I modulating compounds; measuring luciferase activation; and selecting a compound that activates luciferase above a selected threshold in the presence of one or more viral countermeasures. In one embodiment, the selected threshold may be two, three, four or five standard deviations above the control level.

The disclosure further provides methods of identifying compounds that modulate the activity of RIG-I, wherein a compound is structurally selected for predicted binding to the ligand-binding domain of RIG-I, following which the method comprises the steps of providing cells comprising a luciferase reporter gene under the control of a promoter; contacting the cells with putative RIG-I modulating compounds; measuring luciferase activation; and selecting a compound that activates luciferase above a selected threshold in the presence of one or more viral countermeasures. In another embodiment, the selected threshold may be two, three, four or five standard deviations above the control level.

In another embodiment the disclosure provides methods of identifying compounds that modulate the activity of RIG-I from a diversity library of drug-like molecules wherein the method comprises the steps of providing cells comprising a luciferase reporter gene under the control of a promoter; contacting the cells with putative RIG-I modulating compounds; measuring luciferase activation; and selecting a compound that activates luciferase above a selected threshold in the presence of one or more viral countermeasures. In another embodiment, the selected threshold may be two, three, four or five standard deviations above the control level.

The disclosure also relates to methods of identifying compounds that modulate the RIG-I pathway in a vertebrate cell, wherein the modulation is activation.

The disclosure further relates to methods of identifying compounds having at least one activity of activating interferon regulatory factor-3 (IRF-3), inducing the expression of interferon and interferon-stimulated genes (ISGs), and having antiviral activity against at least one of influenza A virus, West Nile virus and Hepatitis C virus.

Negative control cells that did not contain drug are shown in the left panel, cells treated with KIN101 (10 µM) are shown in the middle and cells treated with IFN-β are shown on the right. The infected cells were quantitated using the Array Scan (G). Infected Influenza virus infected cells were measured on the Array Scan and the relative number of infected cells following drug treatment is shown (H).

Figure 10:
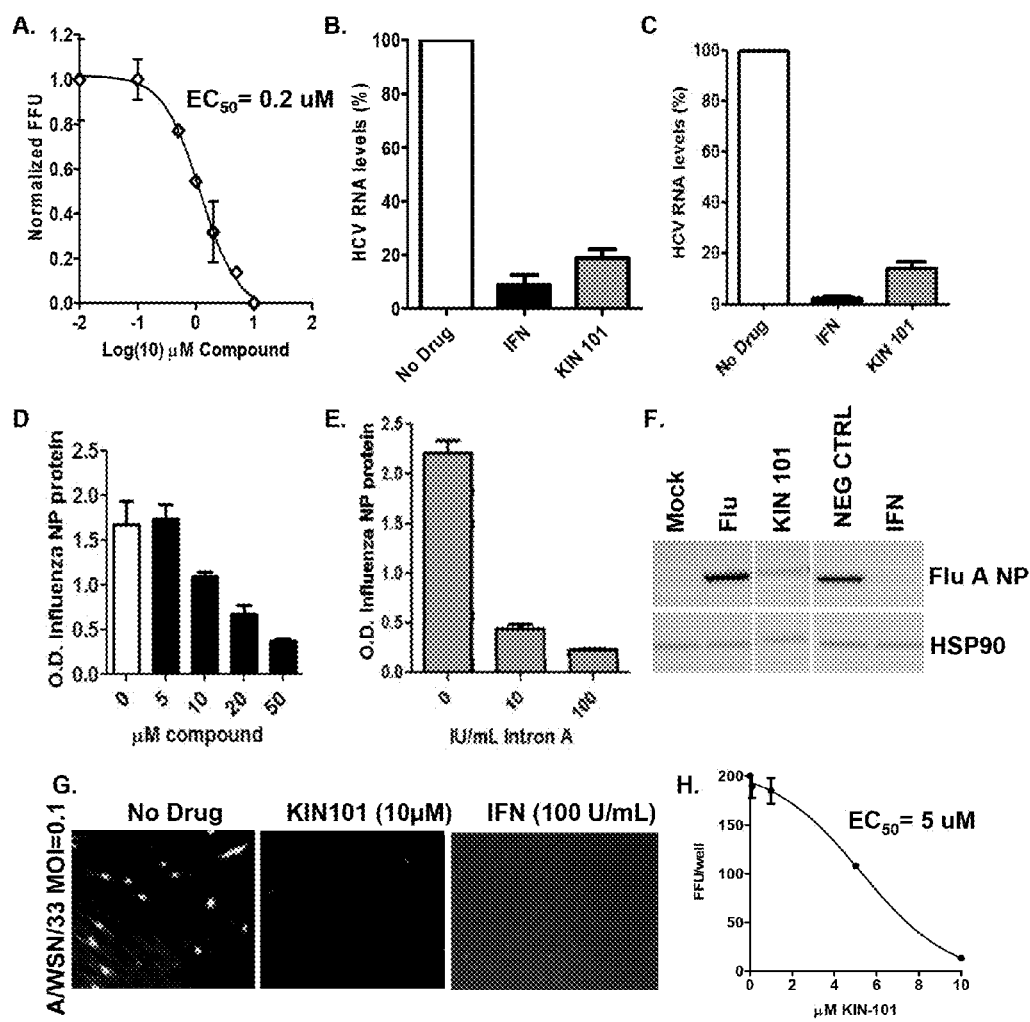
FIG. 10 shows antiviral activity of KIN101. Huh7 cells were treated with KIN101 for 24 h and then infected with HCV-2a at a MOI of 1.0. Cells were grown for an additional 48 h and then stained for HCV proteins. The number of infected cells versus concentration of drug added is shown (A). Huh7 cells were pre-treated with KIN101 (10 μM) and grown for 18 h, cells were then infected with HCV-2a at a MOI of 1.0 and grown for an additional 72 h. Supernatants from infected cells were harvested and HCV RNA was purified and quantified using Real Time PCR with HCV-specific primers. Cells infected with HCV that did not receive KIN101 (untreated) were used as a negative control and values set to 100% infection. IFN-β (Intron A; 100 IU/ml) was used as a positive control for HCV inhibition (B). Huh7 cells were infected with HCV-2a at a MOI of 1.0 and 4 h following infection compounds or IFN were added to infected cells. The remainder of the experiment was done as described in panel B (C). MRC5 cells were pre-treated with increasing doses of KIN101 for 4 h, infected with influenza A virus WSN at a MOI of 1.0 and grown for 24 h. Infected cells were detected using an ELISA method against the influenza virus NP protein. Infected cells with no drug treatment were used as a positive control for infection (D). IFN-β was used as a positive control for antiviral activity. Cells were treated with indicated doses of IFN-β, infected with influenza virus, and infected cells were detected using the ELISA method (E). MRC5 cells were treated and infected as described for panel D. Cells were harvested 24 h after infection, lysed, and whole-cell protein lysates were analyzed by Western blot for the influenza virus NP protein. Mock-infected cells were used to determine nonspecific background and influenza virus infected cells with no drug treatment served as a positive control for infection and detection. IFN was used a positive control for inhibition of influenza virus infection. Bottom panel shows staining with Hsp90 as a loading control (F). MRC5 cells were treated and infected as described in panel D. Sixteen hours post infection, the cells were fixed and the influenza virus NP was detected using specific and fluorescent-tagged antibodies.
Figure 11:
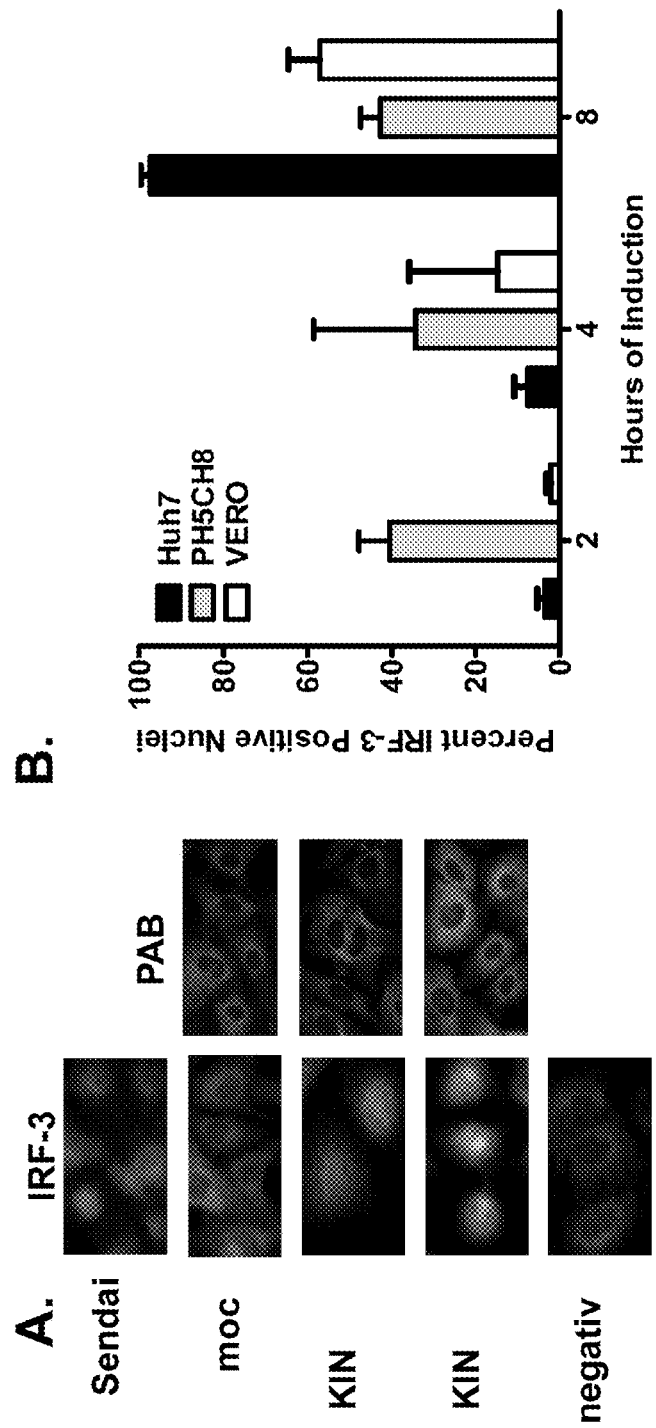

FIG. 11 shows induction of IRF-3 nuclear translocation by KIN100 and KIN101. Huh7 cells (human liver carcinoma) were treated with drug or controls for 18 h, fixed and stained with IRF-3 polyclonal rabbit serum and a FITC secondary antibody (left panel, 'IRF-3'). Mock-infected cells were treated with vehicle alone (0.5% DMSO media) and Sendai virus infection served as a positive control for causing IRF-3 nuclear translocation. KIN101 and KIN100 were added to cells in media containing 0.5% DMSO at a concentration of 10 µM as well as the negative samples that were treated with a drug that showed no activity in screening or validation assays for ISG induction. Cells shown in the right hand panel were treated in a similar fashion and stained for poly (A) binding protein (PABP) as a control for a cytoplasmic protein whose cellular distribution should not be altered by drug treatment (A). Quantitation of IRF-3 translocation in various cell types and different treatment times. Various cell types were treated with negative controls or KIN101 as done in FIG. 10A for the amount of time indicated. Following IRF-3 staining, the cells were analyzed using an Array Scan VTI instrument to quantitate the IRF-3 in the defined nucleus and cytoplasmic regions of the cells. Cells that were positive for IRF-3 nuclear staining were determined by measuring the IRF-3 specific stain intensity and quantitation represents the average of triplicate wells with 100 cells per well analyzed. Cells positive for IRF-3 nuclear localization had three standard deviations more IRF-3 staining in the nucleus than the negative control (B).

FIGS. 12A-12C show induction of IRF-3 nuclear translocation by KIN101 in the presence of viral countermeasure. Human osteosarcoma cells were stably transformed with the HCV NS3-4A protease coding sequence under control of a tetracycline-repressible promoter. Cells were grown in the absence of tetracycline to induce high levels of HCV protease (FIG. 12A). Cells are grown with or without tetracycline and treated with KIN101 (10 µM) or controls for 18 h. Cells were stained for IRF-3 as done in FIG. 11 and representative images are shown (FIG. 12B). Sendai virus infection was used as a control for IRF-3 translocation that is inhibited by HCV NS3-4A protease. Mock-treated cells were grown in media containing 0.5% DMSO C. Images were analyzed on the Array Scan VTI as done in FIG. 11. Values shown demonstrate IRF-3 intensity in the nucleus and represent the average of triplicate wells with 100 cells per well analyzed (FIG. 12C).

FIG. 13 shows expression of discrete immune pathways centered on IRF signaling induced by KIN101. Top signaling pathways up-regulated in MRC5 cells following treatment with KIN101 (A). Network diagram generated using Ingenuity Pathway Analysis showing an interconnected network of genes encoding innate immune proteins up-regulated by KIN101 treatment (B). TaqMan confirmation of selected genes that were shown by microarray to be up-regulated by KIN101 treatment. Normalized expression is shown on a logarithmic scale (C). Western blot analysis showing the increased abundance of proteins downstream of IRF activation following KIN101 treatment. IFN-β treatment was used as a positive control (D).

Figure 14:
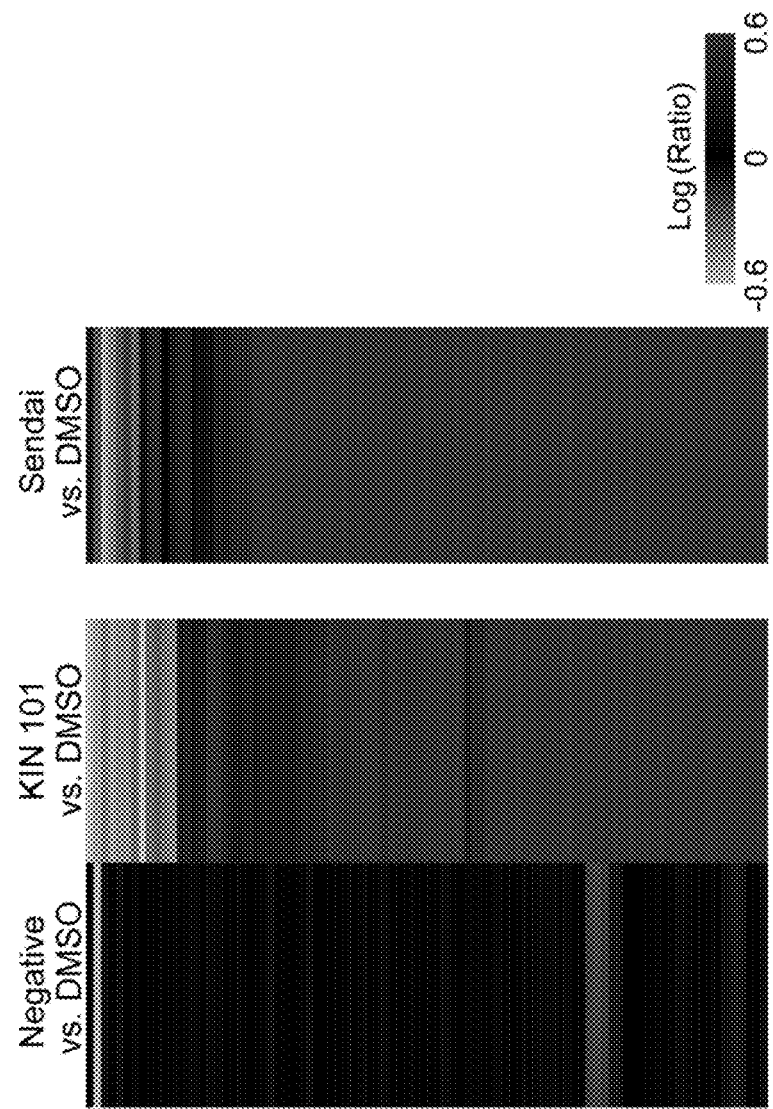

FIG. 14 shows differential gene expression induced by KIN101 compared to mock-treated (DMSO) or Sendai virus infected human MRC5 cells. Genes that exhibited >2-fold change are shown. The profile of up-regulated (red) and down-regulated genes by KIN101 treatment (center column, "KIN101 vs. DMSO") show a pattern similar to Sendai virus infection (right column, "Sendai vs. DMSO"). In contrast, a compound with no activity (left column, "Negative vs. DMSO") has a distinctly different gene expression profile.

FIG. 15 shows the top 20 probes (corresponding to 18 genes) that were up-regulated following treatment with KIN101 compared with that seen in control cells treated with DMSO alone.

FIG. 16 shows the 75 differentially expressed genes from KIN101 treated MRC5 cells as compared with DMSO control treatment.

Figure 17:
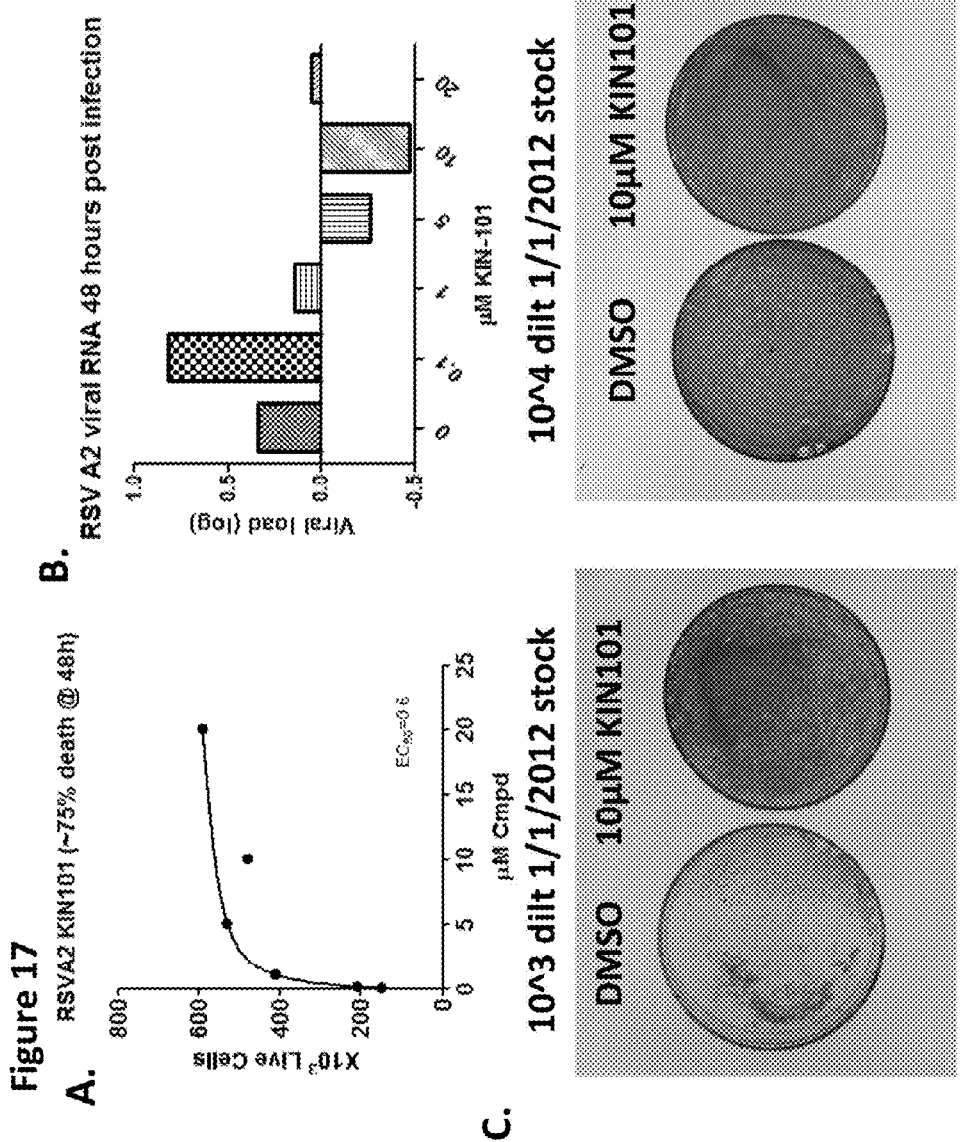

FIG. 17 shows that compounds identified by the described methods significantly inhibit respiratory syncitial virus (RSV). KIN 101 protects cells from RSV-induced cytopathic effects and cell death (panel A), decreases the amount of RSV viral RNA produced by infected cells (panel B), and decreases the number and size of viral induced plaques (panel C).

Figure 18:
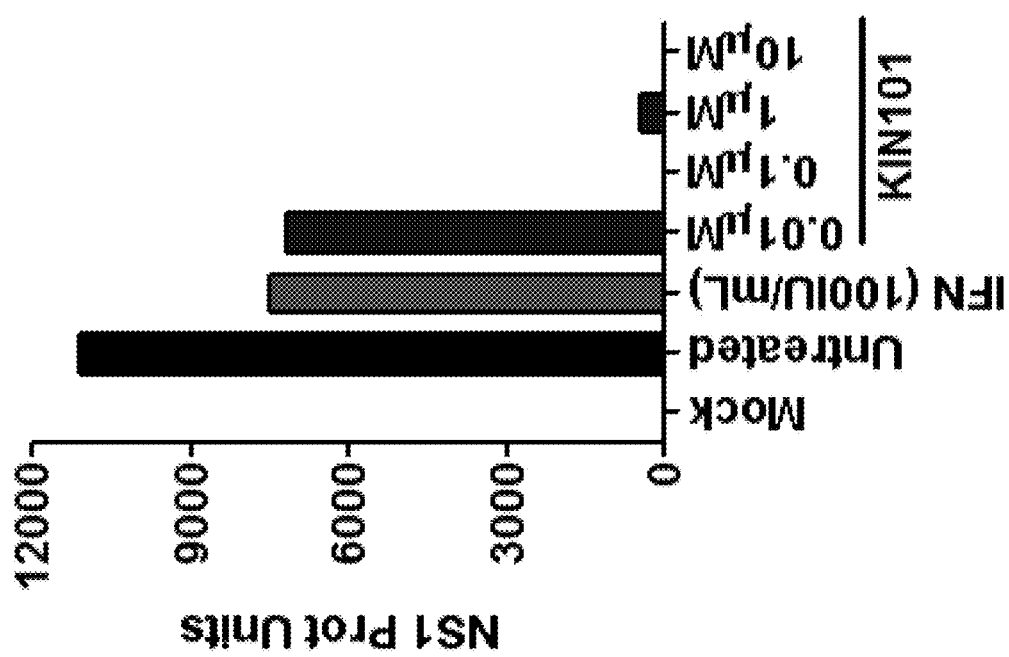

FIG. 18 shows that compounds identified by described methods cause a potent and effective decrease in Dengue virus infection and growth.

DEFINITIONS

As used herein, either alone or in combination, the terms "alkyloxy" or "alkoxy" refer to a functional group comprising an alkyl ether group. Examples of alkoxys include, without limitation, methoxy, ethoxy, n-propoxy, isopropoxy, n-butoxy, iso-butoxy, sec-butoxy, tert-butoxy, and the like.

The terms "alkyl", "alkenyl", and "alkynyl" refer to substituted and unsubstituted alkyls, alkenyls and alkynyls. The term "alkyl" refers to a functional group comprising a straight-chain or branched-chain hydrocarbon containing from 1 to 20 carbon atoms linked exclusively by single bonds and not having any cyclic structure. An alkyl group may be optionally substituted as defined herein. Examples of alkyl groups includes, without limitation methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl, eicosyl, and the like.

Substituted alkyls, alkenyls and alkynyls refers to alkyls, alkenyls and alkynyls substituted with one to five substituents from the group including H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, F, 1-amidine, 2-amidine, alkylcarbonyl, morpholinyl, piperidinyl, dioxanyl, pyranyl, heteroaryl, furanyl, thiophenyl, tetrazolo, thiazolyl, isothiazolyl, imidazolyl, thiadiazolyl, thiadiazole S-oxide, thiadiazole S,S-dioxide, pyrazolo, oxazolyl, isoxazolyl, pyridinyl, pyrimidinyl, quinolinyl, isoquinolinyl, SR, SOR, $SO_2R$, CO2R, COR, CONR'R", CSNR'R", SOnNR'R".

As used herein, either alone or in combination, the term "alkynyl" refers to a functional group comprising a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like.

The term "alkylene," as used herein, alone or in combination, refers to a saturated aliphatic group derived from a straight or branched chain saturated hydrocarbon attached at two or more positions, such as methylene (—C2-). Unless otherwise specified, the term "alkyl" may include "alkylene" groups.

As used herein, either alone or in combination, the term "alkylcarbonyl" or "alkanoyl" refers to a functional group comprising an alkyl group attached to the parent molecular moiety through a carbonyl group. Examples of alkylcarbonyl groups include, without limitation, methylcarbonyl, ethylcarbonyl, and the like.

The term "alkynylene" refers to a carbon-carbon triple bond attached at two positions such as ethynylene (—C:::C—, —C≡C—). Unless otherwise specified, the term "alkynyl" may include "alkynylene" groups.

As used herein, either alone or in combination, the term "aryl", "hydrocarbyl aryl", or "aryl hydrocarbon" refers to a functional group comprising a substituted or unsubstituted aromatic hydrocarbon with a conjugated cyclic molecular ring structure of 3 to 12 carbon atoms. An aryl group can be monocyclic, bicyclic or polycyclic, and may optionally include one to three additional ring structures, such as, e.g., a cycloalkyl, a cycloalkenyl, a heterocycloalkyl, a heterocycloalkenyl, or a heteroaryl. The term "aryl" includes, without limitation, phenyl (benzenyl), thiophenyl, indolyl, naphthyl, totyl, xylyl, anthracenyl, phenanthryl, azulenyl, biphenyl, naphthalenyl, 1-mMethylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl. Substituted aryl refers to aryls substituted with one to five substituents from the group including H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR, SOR, $SO_2R$, $CO_2R$, COR, CONRR, CSNRR, SOnNRR.

As used herein, either alone or in combination, the term "lower aryl" refers to a functional group comprising a substituted or unsubstituted aromatic hydrocarbon with a conjugated cyclic molecular ring structure of 3 to 6 carbon atoms. Examples of lower aryl groups include, without limitation, phenyl and naphthyl.

As used herein, either alone or in combination, the term "carboxyl" or "carboxy" refers to the functional group —C(═O)OH or the corresponding "carboxylate" anion —C(═O)O—. Examples include, without limitation, formic acid, acetic acid, oxalic acid, benzoic acid. An "O-carboxyl" group refers to a carboxyl group having the general formula RCOO, wherein R is an organic moiety or group. A "C-carboxyl" group refers to a carboxyl group having the general formula COOR, wherein R is an organic moiety or group.

As used herein, either alone or in combination, the term "cycloalkyl", "carbocyclicalkyl", and "carbocyclealkyl" refers to a functional group comprising a substituted or unsubstituted non-aromatic hydrocarbon with a non-conjugated cyclic molecular ring structure of 3 to 12 carbon atoms linked exclusively with carbon-carbon single bonds in the carbon ring structure. A cycloalkyl group can be monocyclic, bicyclic or polycyclic, and may optionally include one to three additional ring structures, such as, e.g., an aryl, a heteroaryl, a cycloalkenyl, a heterocycloalkyl, or a heterocycloalkenyl.

As used herein, either alone or in combination, the term "lower cycloalkyl" refers to a functional group comprising a monocyclic substituted or unsubstituted non-aromatic hydrocarbon with a non-conjugated cyclic molecular ring structure of 3 to 6 carbon atoms linked exclusively with carbon-carbon single bonds in the carbon ring structure. Examples of lower cycloalkyl groups include, without limitation, cyclopropyl, cyclobutyl, cyclopentyl, and cyclohexyl.

As used herein, the term "functional group" refers to a specific group of atoms within a molecule that are responsible for the characteristic chemical reactions of those molecules.

As used herein, either alone or in combination, the term "heteroalkyl" refers to a functional group comprising a straight-chain or branched-chain hydrocarbon containing from 1 to 20 atoms linked exclusively by single bonds, where at least one atom in the chain is a carbon and at least one atom in the chain is O, S, N, or any combination thereof. The heteroalkyl group can be fully saturated or contain from 1 to 3 degrees of unsaturation. The non-carbon atoms can be at any interior position of the heteroalkyl group, and up to two non-carbon atoms may be consecutive, such as, e.g., —CH2-NH—OCH3. In addition, the non-carbon atoms may optionally be oxidized and the nitrogen may optionally be quaternized.

As used herein, either alone or in combination, the term "heteroaryl" refers to a functional group comprising a substituted or unsubstituted aromatic hydrocarbon with a conjugated cyclic molecular ring structure of 3 to 12 atoms, where at least one atom in the ring structure is a carbon and at least one atom in the ring structure is O, S, N, or any combination thereof. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups include, without limitation, acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like.

As used herein, either alone or in combination, the term "lower heteroaryl" refers to a functional group comprising a monocyclic or bicyclic, substituted or unsubstituted aromatic hydrocarbon with a conjugated cyclic molecular ring structure of 3 to 6 atoms, where at least one atom in the ring structure is a carbon and at least one atom in the ring structure is O, S, N, or any combination thereof.

As used herein, either alone or in combination, the term "hydroxy" refers to the functional group hydroxyl (—OH).

As used herein, either alone or in combination, the term "oxo" refers to the functional group =O.

As used herein, the term "vertebrate" includes all living vertebrates such as, without limitation, mammals, humans, birds, dogs, cats, livestock, farm animals, free-range herds, etc.

DETAILED DESCRIPTION

The present disclosure provides methods to identify compounds that shift the focus of viral treatments away from the targeting of viral proteins to the development of drugs that target and enhance the host (patient's) innate antiviral response. Such compounds and methods are likely to be more effective, less susceptible to the emergence of viral resistance, cause fewer side effects and be effective against a range of different viruses (1).

The RIG-I pathway is intimately involved in regulating the innate immune response to RNA virus infections. RIG-I is a cytosolic pathogen recognition receptor that is essential for triggering immunity to a wide range of RNA viruses (5-8). RIG-I is a double-stranded RNA helicase that binds to motifs within the RNA virus genome characterized by homopolymeric stretches of uridine or polymeric U/A motifs (9). Binding to RNA induces a conformation change that relieves RIG-I signaling repression by an autologous repressor domain, thus allowing RIG-I to signal downstream through its tandem caspase activation and recruitment domains (CARDs) (4). RIG-I signaling is dependent upon its NTPase activity, but does not require the helicase domain (10, 11). RIG-I signaling is silent in resting cells, and the repressor domain serves as the on-off switch that governs signaling in response to virus infection (8).

RIG-I signaling is transduced through IPS-1 (also known as Cardif, MAVs, and VISA), an essential adaptor protein that resides in the outer mitochondrial membrane (12-15). IPS-1 recruits a macromolecular signaling complex that stimulates the downstream activation of IRF-3, a transcription factor that induces the expression of type I IFNs and virus-responsive genes that control infection (16). Compounds that trigger RIG-I signaling directly or through modulation of RIG-I pathway components, including IRF-3, present attractive therapeutic applications as antivirals or immune modulators.

RIG-I signaling is a target for viral countermeasures which result in cleavage of signaling components and a resulting down-regulation of innate immune signaling that blocks viral clearance and favors a persistent infection. As used herein, viral countermeasures refer to any viral protein, nucleic acid, or structure that has an effect within a cell including inhibiting one or more cellular anti-viral activities. RNA viruses utilize several mechanisms of countermeasures that are listed in the following Table 1.

TABLE 1

Examples of viral countermeasures that could be used in compound screening methods disclosed herein.

| Virus | Viral Protein | Cellular target within RIG-I pathway | GENBANK ID |
|---|---|---|---|
| Hepatitis C virus | NS3/4a | IPS-1 | AY46460.1 (SEQ ID NO: 1) |
| GBV-B | NS3/4a | IPS-1 | AF179612.1 (SEQ ID NO: 2) |
| Hepatitis A virus | 3ABC | IPS-1 | M14707.1 (SEQ ID NO: 3) |
| Paramyxovirus | V protein | MDA-5 | AF079780.2 (SEQ ID NO: 4) |
| Influenza A virus | NS1 | RIG-I | 956533 (SEQ ID NO: 5) |
| Ebola virus | VP35 | IRF-3 activation | 955189 (SEQ ID NO: 6) |
| Respiratory syncytial virus | NS1, NS2 | IRF-3 activation | 1494468; 1494469 (SEQ ID NOs: 7 and 8) |

One approach to overcome these mechanisms is to select for compounds that activate the RIG-I pathway in the presence of viral proteins or countermeasures. Non-limiting examples described herein allow the identification of compounds that efficiently activate IRF-3 and resulting promoters such as IFN and ISG in the presence of HCV NS34A protease which is known to block IPS-1 signaling within the RIG-I pathway.

Methods to develop additional reporter cell lines that express other viral countermeasures for use in high throughput screening are also disclosed herein. In a non-limiting example, reporter U2OS cell lines are developed to stably express each viral countermeasure protein as listed in Table 1 under control of tetracycline and Firefly luciferase utilizing the IFN-β promoter. The viral countermeasure protein is expressed under the control of a Tetracycline-repressive promoter, and in the presence of Tetracycline do not express the protein. These cell lines are responsive to RIG-I mediated stimulus including Sendai virus infection as well as IFN treatment and are utilized to identify RIG-I agonists through high throughput screening (HTS) of a small molecule library. Induction of reporter cell lines are optimized for cell growth and assay conditions that are used in the HTS to obtain the most sensitive and reproducible results. Additionally, a control cell line that expresses Renilla luciferase using the actin promoter is a negative control. The actin cell line is utilized in a counter screen to identify compounds that cause nonspecific changes in global gene expression.

Cloning of viral countermeasure protein encoding gene constructs. Sequences are obtained from Genbank ID numbers listed in Table 1.

Cloning of IFN-β and β-actin promoter constructs: Actin promoter sequence was amplified from stock genomic DNA using the following primers:

```
                                      (SEQ ID NO: 9)
Actin 5' SacI:    GGGAGCTCCCCAAGGCGGCCAAC (SEQ ID NO: 10)
Actin 3' HindIII: GGAAGCTTGGTCTCGGCGGTGGT
```

The IFN-β promoter including the following sequence:

(SEQ ID NO: 11)
CTAAAATGTAAATGACATAGGAAAACTGAAAGGGAGAAGTGAAAGTGGGA

AATTCCTCTGAATAGAGAGAGGACCATCTCATATAAATAGGCCATACCCA

TGGAGAAAGGACATTCTAACTGCAACCTTTCG was inserted into the pGL4.14 luciferase construct (available from Promega Inc.) using a SacI and HindIII restriction sites at the 5' and 3' ends respectively.

The sequence fragments were amplified using Platinum PCR reactions. The PCR fragments were purified, digested with SacI and EcoRV or HindIII and ligated into the Promega luciferase vectors. The actin promoter sequence was ligated into the pGL4.76 vector which contains a hygromycin selectable marker. IFN-β promoter sequences were inserted into the pGL4.14 vector that contains a hygromycin selectable marker. Constructs were confirmed by sequencing and plasmid maps.

Production of stable cell lines: U2OS cells that stably expressed the viral countermeasure under control of the Tet-repressive promoter are seeded in a 6-well plate at $2.5 \times 10^5$ cells and grown overnight under normal growth conditions prior to transfection. Cells are transfected with 2 µg of the vector DNA using Lipofectin and Plus Reagent from Invitrogen. Transfections are done using suggested reagent volumes and ratios provided in the Invitrogen protocol. Following transfection, cells are grown to confluency (24-48 hours) and each well is then split into two 10 cm dishes. Cells are grown 24 hours and then media is replaced with selective media containing the appropriate antibiotic. The optimal concentration of antibiotics for U2OS cells was determined to be 400 µg/mL G418 and 250 µg/mL Hygromycin. Cells are grown in the presence of antibiotic until 80% of cells die under selective pressure and individual colonies appear. When colonies contain >50 cells they are trypsinized from the plate, transferred to a 96-well plate and grown in the presence of antibiotic (only 20-40% of the clones survive this phase). Surviving clones are grown and passaged when they reach 80% confluency under normal conditions but with media containing antibiotic. All stable cell line clones are tested for optimal induction of IFN-β in the presence of viral countermeasure expression.

A high-throughput screening approach was used to identify compounds that modulate the RIG-I pathway in the presence of viral countermeasures. Validated RIG-I agonist lead compounds were demonstrated to specifically activate interferon regulatory factor-3 (IRF-3). They also induce the expression of interferon-stimulated genes (ISGs), have low cytotoxicity in cell-based assays, are suitable for analog development and QSAR studies, have drug-like physiochemical properties, and have antiviral activity against influenza A virus and/or hepatitis C virus (HCV). As discussed below, these compounds represent a new class of potential antiviral therapeutics. Although the disclosure is not bound by a specific mechanism of action of the compounds in vivo, the compounds are selected for their modulation of the RIG-I pathway. In certain embodiments, the modulation is activation of the RIG-I pathway.

Antiviral and mechanistic actions of lead compounds were used to identify a list of validated compounds suitable for optimization and pharmaceutical development. Experiments focused on HCV, influenza virus, and West Nile virus.

Lead compounds disclosed herein function to decrease viral protein, viral RNA, and infectious virus in cell culture models of HCV and influenza virus.

Many RNA viruses share biochemical, regulatory, and signaling pathways. These viruses include but are not limited to influenza virus (including avian and swine isolates), Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and the Kyasanur forest disease virus. The methods described herein can be used to identify compounds that can be used to treat these viruses.

Relevant taxonomic families of RNA viruses include, without limitation, Astroviridae, Birnaviridae, Bromoviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, and Tymoviridae. The compounds and methods disclosed herein can be used to treat these families of viruses. Methods disclosed herein can also used to identify compounds effective against DNA viruses and the use of the methods for this purpose are expressly included within the current disclosure. Compounds identified by methods disclosed herein that are effective against DNA viruses can be used to treat vertebrates afflicted with the DNA virus.

The disclosure also provides methods of identifying a therapeutic compound for preventing or inhibiting infection by a virus, wherein the therapeutic compound has the structure:

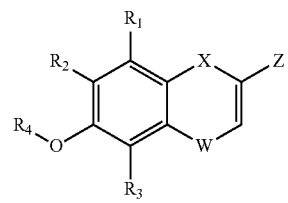

wherein $R_1$, $R_2$ and $R_3$ (independently) are H, lower alkyl, aryl, alkenyl, alkynyl, alkylaryl, arylalkyl, alkoxy, aryloxy, arylalkoxy, alkoxyalkylaryl, alkylamino, arylamino, heteroalkyl, heteroaryl, cyclic heteroalkyl, acyl, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, $SR_5$, $SOR_6$, $SO_2R_7$, $CO_2R_8$, $COR_9$, $CONR_{10}R_{11}$, $CSNR_{12}R_{13}$, $SO_nNR_{14}R_{15}$, $R_4$ (independently) is H, lower alkyl, aryl, alkenyl, alkynyl, alkylaryl, arylalkyl, alkoxyalkylaryl, alkylamino, arylamino, heteroalkyl, heteroaryl, cyclic heteroalkyl, acyl, alkylsulfonyl, arylsulfonyl and heterocyclicalkylalkyl, W is O or NH, X is C=O, S=O or $SO_2$, and Z is alkyl substituted alkyl, aryl, substituted aryl, heteroalkyl, heteroaryl, substituted heteroaryl, arylalkyl, heteroaryl alkyl.

Exemplary compounds include

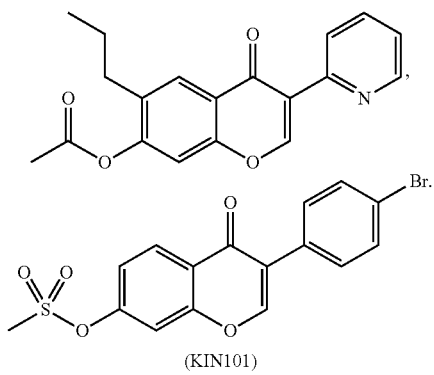

(KIN101)

The compounds and methods disclosed herein can be additive or synergistic with other therapies currently in development or use. For example, ribavirin and interferon-α provide an effective treatment for HCV infection when used in combination. Their efficacy in combination can exceed the efficacy of either drug product when used alone. The compositions of the disclosure can be administered alone or in combination or conjunction with interferon, ribavirin and/or a variety of small molecules that are being developed against both viral targets (viral proteases, viral polymerase, assembly of viral replication complexes) and host targets (host proteases required for viral processing, host kinases required for phosphorylation of viral targets such as NS5A, and inhibitors of host factors required to efficiently utilize the viral internal ribosome entry site, or IRES).

The disclosure provides for a vaccine comprised of the identified compounds, alone or in combination with an antigen, for the purpose of preventing or treating disease in an animal including a vertebrate animal.

The disclosure provides for the use of the compounds as adjuvants.

The compounds and methods disclosed herein could be used in combination or conjunction with, without limitation, adamantane inhibitors, neuraminidase inhibitors, alpha interferons, non-nucleoside or nucleoside polymerase inhibitors, NS5A inhibitors, antihistamines, protease inhibitors, helicase inhibitors, P7 inhibitors, entry inhibitors, IRES inhibitors, immune stimulators, HCV replication inhibitors, cyclophilin A inhibitors, A3 adenosine agonists, and micro-RNA suppressors. Several direct acting antivirals are in development for the treatment of Hepatitis C virus and are being clinically tested in combination with existing therapies. The immune acting compounds disclosed herein could be administered in combination or conjunction with the Hepatitis C virus drugs listed in Table 2 without limitation.

TABLE 2

Hepatitis C virus drugs in development

| Mechanism of action | Generic Name | Manufacturer |
| --- | --- | --- |
| Protease inhibitor | Boceprevir | Merck |
| Protease inhibitor | Telaprevir | Vertex |
| BMS 790052 | NS5A Inhibitor | Bristol-Myers Squibb |
| ANA598 | Polymerase Inhibitor | Anadys Pharmaceuticals |
| BI 201335 | Protease Inhibitor | Boehringer Ingelheim Pharma |
| BI 207127 | Polymerase Inhibitor | Boehringer Ingelheim Pharma |
| BMS 650032 | Protease Inhibitor | Bristol-Myers Squibb |
| BMS 790052 | NS5A Inhibitor | Bristol-Myers Squibb |
| BMS 791325 | Polymerase Inhibitor | Bristol-Myers Squibb |
| Filibuvir | Polymerase Inhibitor | Pfizer |
| GS9190 (Tegobuvir) | Polymerase Inhibitor | Gilead |
| GS-9256 | Protease Inhibitor | Gilead |
| PSI-7977 | Polymerase Inhibitor | Pharmasset |
| RG7128 | Polymerase Inhibitor | Pharmasset/Genentech |
| RG7227 (Danoprevir) | Protease Inhibitor | InterMune/Genentech |
| SCH900518 (Narlaprevir) | Protease Inhibitor | Merck |
| TMC435 | Protease Inhibitor | Medivir/Tibotec |
| Vaniprevir (MK-7009) | Protease Inhibitor | Merck |
| VX-222 | Polymerase Inhibitor | Vertex |

Additional combination therapies could include a compound identified by the methods disclosed herein with one or more of the drugs listed in Tables 2.5 & 2.7.

TABLE 2.5

HCV Drugs in Development

| Target | Drug |
| --- | --- |
| 3' UTR | RNAi Clevage HCV Genome: TT-033 |
| NS5B | Polymerase Inhibitors: NM107, PSI-879, PSI-661, IDX-184, IDX-375, PSI-7851, PSI-938, VX-759, INX-189, ABT-072, ABT-333, ANA-598, GS-9190, PSI-7977, PF-00868554, RG-7128, VX-222 |
| NS5A | NS5A Inhibitors: A-832, BMS-790052 |
| NS4B | Antihistamine: Clemizole |
| NS4A NS3 | Protease Inhibitor: AVL-181, VX-813, , ACH-1625, IDX-320, MK-5172, PHX-1766, VX-500, VX-985, BI-201335, BMS-650032, MK-7009, ITMN-191/R7227, SCH-900518, TMC-435350, GS-9256, Bocepravir, Telapravir; Helicase Inhibitors: BTN10, BTN11, Trixsalen |
| P7 | P7 Inhibitors: BIT225 |
| E2 | Entry Inhibitors: ITX-4520, ITX-5061 |
| 5' UTR | IRES Inhibitors: DNAzymes, HH-363-50 |
| Immune Stimulators | Glycosylated interferon: Glycoferon; Interferon Type 1: ITCA-638; Toll-Like Receptor Agonists: ANA-773, IMO-2125; Interferon: PEG interferon lambda, Locteron; Toll-Like Receptor Agonists: R-848; 5' T-cell Agonist: IPH-1011; STAT-3 Inhibitor: SCV-07; Ag stimulate T-Cells: GI-5005; Interlukin-7: CYT-107 |

TABLE 2.5-continued

HCV Drugs in Development

| Target | Drug |
|---|---|
| Host Cell Factors | Cyclophilin A Inhibitor: NIM-811; SCY-635; A3 Adenosine Agonist: CF102; microRNA Supressor: SPC3649/LNA antimiR-22; Anti-Phosphatidylserine Ab: Bavituximab; Anti-PD1 Ab: MDX-1106; Cyclophilin A Inhibitor: Debio-025; Alpha-1 Glucosidase Inhibitor: Celogsivir |
| Ribavirin | Prodrug Ribavirin: Taribavirin |
| Other | HCV Replication Inhibitor: ATI-0810; Thiazolide: Nitazoxanide/Alina |

TABLE 2.7

Influenza and West Nile Virus Drugs in Development

| Drug Class Description | Drug |
|---|---|
| Neuraminidase Inhibitors | Peramivir; Laninamivir |
| Triple Therapy - Neuraminidase Inhibitor, ribavirin, amantadine | ADS-8902 |
| Polymerase Inhibitors | Favipiravir |
| Reverse Transcriptase Inhibitor | ANX-201 |
| Inhaled Chitosan | ANX-211 |
| Entry/Binding Inhibitors | Binding Site Mimetic: Flucide; Entry Inhibitor: Fludase; Fusion Inhibitor: MGAWN1 (West Nile) |
| Host Cell Inhibitors | Iantibiotics |
| Cleavage of RNA genome | RNAi: Unnamed; RNAse L: Unnamed |
| Immune Stimulators | Interferon: Alferon-LDO; Alferon N (West Nile); Neukokinin1 agonist: Homspera |
| Unknown | TG21 |

Cytokines that could be administered in combination or conjunction with the compounds and methods disclosed herein include, without limitation, IL-2, IL-12, IL-23, IL-27, or IFN-γ. New HCV drugs that are or will be available for potential administration in combination or conjunction with the compounds and methods disclosed herein include, without limitation, ACH-1625 (Achillion); Glycosylated interferon (Alios Biopharma); ANA598, ANA773 (Anadys Pharm); ATI-0810 (Arisyn Therapeutics); AVL-181 (Avila Therapeutics); LOCTERON® (Biolex); CTS-1027 (Conatus); SD-101 (Dynavax Technologies); Clemizole (Eiger Biopharmaceuticals); GS-9190 (Gilead Sciences); GI-5005 (GlobalImmune BioPharma); Resiquimod/R-848 (Graceway Pharmaceuticals); Albinterferon alpha-2b (Human Genome Sciences); IDX-184, IDX-320, IDX-375 (Idenix); IMO-2125 (Idera Pharmaceuticals); INX-189 (Inhibitex); ITCA-638 (Intarcia Therapeutics); ITMN-191/RG7227 (Intermune); ITX-5061, ITX-4520 (iTherx Pharmaceuticals); MB11362 (Metabasis Therapeutics); Bavituximab (Peregrine Pharmaceuticals); PSI-7977, RG7128, PSI-938 (Pharmasset); PHX1766 (Phenomix); Nitazoxanide/ALINIA® (Romark Laboratories); SP-30 (Samaritan Pharmaceuticals); SCV-07 (SciClone); SCY-635 (Scynexis); TT-033 (Tacere Therapeutics); Viramidine/taribavirin (Valeant Pharmaceuticals); Telaprevir, VCH-759, VCH-916, VCH-222, VX-500, VX-813 (Vertex Pharmaceuticals); and PEG-INF Lambda (Zymogenetics).

New influenza and West Nile virus drugs that are or will be available for potential administration in combination or conjunction with the compounds and methods disclosed herein include, without limitation, neuraminidase inhibitors (Peramivir, Laninamivir); triple therapy—neuraminidase inhibitors ribavirin, amantadine (ADS-8902); polymerase inhibitors (Favipiravir); reverse transcriptase inhibitor (ANX-201); inhaled chitosan (ANX-211); entry/binding inhibitors (Binding Site Mimetic, Flucide); entry inhibitor, (Fludase); fusion inhibitor, (MGAWN1 for West Nile); host cell inhibitors (lantibiotics); cleavage of RNA genome (RNAi, RNAse L); immune stimulators (Interferon, Alferon-LDO; Neurokinin) agonist, Homspera, Interferon Alferon N for West Nile); and TG21.

Other drugs for treatment of influenza and/or hepatitis that are available for potential administration in combination or conjunction with the compounds and methods disclosed herein include, without limitation:

TABLE 3

Hepatitis and influenza drugs

| Branded Name | Generic Name | Approved Indications |
|---|---|---|
| Pegasys | PEGinterferon alfa-2a | Hepatitis C, Hepatitis B |
| Peg-Intron | PEGinterferon alfa-2b | Hepatitis C |
| Copegus | Ribavirin | Hepatitis C |
| Rebetol | Ribavirin | Hepatitis C |
| — | Ribavirin | Hepatitis C |
| Tamiflu | Oseltamivir | Influenza A, B, C |
| Relenza | Zanamivir | Influenza A, B, C |
| — | Amantadine | Influenza A |
| — | Rimantadine | Influenza A |

These agents can be incorporated as part of the same pharmaceutical composition or can be administered separately from the compounds of the disclosure, either concurrently or in accordance with another treatment schedule. In addition, the compounds or compositions of the disclosure can be used as an adjuvant to other therapies.

The compounds and methods disclosed herein can be additive or synergistic with other compounds and methods to enable vaccine development. By virtue of their antiviral and immune enhancing properties, the compounds can be used to affect a prophylactic or therapeutic vaccination. The compounds need not be administered simultaneously or in combination with other vaccine components to be effective. The vaccine applications of the compounds are not limited to the prevention or treatment of virus infection but can encompass all therapeutic and prophylactic vaccine applications due to the general nature of the immune response elicited by the compounds.

As is understood by one of ordinary skill in the art, vaccines can be against viruses, bacterial infections, cancers, etc. and can include one or more of, without limitation, a live attenuated vaccine (LAIV), an inactivated vaccine (IIV; killed virus vaccine), a subunit (split vaccine); a sub-virion vaccine; a purified protein vaccine; or a DNA vaccine.

Appropriate adjuvants include one or more of, without limitation, water/oil emulsions, non-ionic copolymer adjuvants, e.g., CRL 1005 (Optivax; Vaxcel Inc., Norcross, Ga.), aluminum phosphate, aluminum hydroxide, aqueous suspensions of aluminum and magnesium hydroxides, bacterial endotoxins, polynucleotides, polyelectrolytes, lipophilic adjuvants and synthetic muramyl dipeptide (norMDP) analogs such as N-acetyl-nor-muranyl-L-alanyl-D-isoglutamine, N-acetyl-muranyl-(6-O-stearoyl)-L-alanyl-D-isoglutamine or N-Glycol-muranyl-LalphaAbu-D-isoglutamine (Ciba-Geigy Ltd.).

The pharmaceutical composition comprising a compound of the disclosure can be formulated in a variety of forms, e.g., as a liquid, gel, lyophilized, or as a compressed solid. The preferred form will depend upon the particular indication being treated and will be apparent to one of ordinary skill in the art. In one embodiment, the disclosed RIG-I agonists include formulations for oral delivery that can be small-molecule drugs that employ straightforward medicinal chemistry processes The administration of the formulations of the present disclosure can be performed in a variety of ways, including, but not limited to, orally, subcutaneously, intravenously, intracerebrally, intranasally, transdermally, intraperitoneally, intramuscularly, intrapulmonary, intrathecally, vaginally, rectally, intraocularly, or in any other acceptable manner. The formulations can be administered continuously by infusion, although bolus injection is acceptable, using techniques well known in the art, such as pumps (e.g., subcutaneous osmotic pumps) or implantation. In some instances the formulations can be directly applied as a solution or spray.

An example of a pharmaceutical composition is a solution designed for parenteral administration. Although in many cases pharmaceutical solution formulations are provided in liquid form, appropriate for immediate use, such parenteral formulations can also be provided in frozen or in lyophilized form. In the former case, the composition must be thawed prior to use. The latter form is often used to enhance the stability of the active compound contained in the composition under a wider variety of storage conditions, as it is recognized by those or ordinary skill in the art that lyophilized preparations are generally more stable than their liquid counterparts. Such lyophilized preparations are reconstituted prior to use by the addition of one or more suitable pharmaceutically acceptable diluents such as, without limitation, sterile water for injection or sterile physiological saline solution.

Parenterals can be prepared for storage as lyophilized formulations or aqueous solutions by mixing, as appropriate, the compound having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives can be added to retard microbial growth, and are typically added in amounts of about 0.2%-1% (w/v). Suitable preservatives for use with the present disclosure include, without limitation, phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers can be added to ensure isotonicity of liquid compositions and include, without limitation, polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active compound weight.

Additional miscellaneous excipients include bulking agents or fillers (e.g., starch), chelating agents (e.g., EDTA), antioxidants (e.g., ascorbic acid, methionine, vitamin E) and cosolvents.

The active ingredient can also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, cited above.

Parenteral formulations to be used for in vivo administration generally are sterile. This is readily accomplished, for example, by filtration through sterile filtration membranes.

Suitable examples of sustained-release preparations include semi-permeable matrices of solid hydrophobic polymers containing the compound or composition, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the PROLEASE® technology or LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release compounds for shorter time periods.

Oral administration of the compounds and compositions is one intended practice of the disclosure. For oral administration, the pharmaceutical composition can be in solid or liquid form, e.g., in the form of a capsule, tablet, powder, granule, suspension, emulsion or solution. The pharmaceutical composition is preferably made in the form of a dosage unit containing a given amount of the active ingredient. A suitable daily dose for a human or other vertebrate can vary widely depending on the condition of the patient and other factors, but can be determined by persons of ordinary skill in the art using routine methods.

In solid dosage forms, the active compound can be admixed with at least one inert diluent such as sucrose, lactose, or starch. Such dosage forms can also comprise, as is normal practice, additional substances, e.g., lubricating agents such as magnesium stearate. In the case of capsules, tablets and pills, the dosage forms can also comprise buffering agents. Tablets and pills can additionally be prepared with enteric coatings.

The compounds or compositions can be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they can be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

The table below provides non-limiting exemplary viral families, non-limiting exemplary members of the family and non-limiting exemplary species affected by the viral families and its members. These species can be treated for the viruses using compounds identified by the methods described herein.

| Viral Family | Exemplary Members of Viral Family | Affected Animal Species |
|---|---|---|
| Coronaviridae | Avian infectious bronchitis virus | A |
| | Bovine coronavirus | B |
| | Canine coronavirus | C |
| | Feline enteric coronaviruses | F |
| | Feline infectious peritonitis virus | F |
| | Human coronaviruses (colds) | H |
| | Porcine epidemic diarrhea virus | P |
| | Porcine hemagglutinating encephalomyelitis virus | P |
| | Severe acute respiratory syndrome (SARS) virus | H, F |
| | Transmissible gastroenteritis (TGE) virus | P |
| Filoviridae | Ebola virus | H, NHP |
| | Marburg virus | H, NHP |
| Flaviviridae | Border disease virus | O |
| | Bovine viral diarrhea viruses 1, 2 | B |
| | Classical swine fever virus (hog cholera) | P |
| | Dengue virus | H, NHP |
| | Hepatitis C virus | H, NHP |
| | Japanese encephalitis virus | A, P |
| | St. Louis encephalitis virus | H, A, EQ |
| | Tick-borne encephalitis viruses (various subtypes | B, C, O, R |
| | Yellow fever virus | H, NHP |
| | Wesselsbron virus | H, B, CP, O |
| | West Nile virus | H, A, EQ |
| Orthomyxoviridae | Influenza virus A | H, A, EQ, F, FR, P |
| | Avian influenza | H, A, EQ, P |
| | Equine influenza | EQ |
| | Swine influenza | H, A, P |
| | Human influenza | H, FR, P |
| | Influenza virus B (human influenza) | H, FR |
| | Influenza virus C (human influenza) | H, P |
| Paramyxoviridae | Avian paramyxovirus type 1 | H, A |
| | (Newcastle disease) H A | |
| | Avian paramyxoviruses 2-9 A | A |
| | Bovine respiratory syncytial virus (BRSV) | B, O |
| | Canine distemper virus C, Fr | C, FR |
| | Canine parainfluenza virus C | C |
| | Hendra virus | H, BT, EQ, F |

-continued

| Viral Family | Exemplary Members of Viral Family | Affected Animal Species |
|---|---|---|
| | Human parainfluenza viruses 1-4 | H |
| | Measles virus | H, NHP |
| | Mumps virus | H |
| | Nipah virus | H, BT, C, CP, EQ, F, O, P |
| | Parainfluenza 3 virus | H, B, O |
| | Peste de petitis ruminants virus | CP, O |
| | Respiratory syncytial virus | H |
| | Rinderpest virus | B, CP, O, P |
| Picornaviridae | Avian enteroviruses (encephalomyelitis, hepatitis) | A |
| | Bovine enteroviruses | B |
| | Bovine rhinoviruses | B |
| | Encephalomyelocarditis virus (encephalomyelocarditis) | H, NHP, P, R |
| | Equine rhinoviruses 1, 2 | EQ |
| | Foot and mouth disease virus | H, B, CA, CP, CV, O, P |
| | Human hepatitis A virus | H, NHP |
| | Human rhinoviruses | H |
| | Poliovirus | H |
| | Porcine enteroviruses (porcine enteroviral encephalomyelitis/Teschen-Talfan disease) | P |
| | Swine vesicular disease virus | H, P |
| Rhabdoviridae | Bovine ephemeral fever virus | B |
| | Infectious hematopoietic necrosis (IHN) | F |
| | Rabies | F |
| | Spring viremia of carp | H, ALL MAMMALS |
| | Vesicular stomatitis virus (Indiana 1 and New Jersey subtypes) | H, B, CP, EQ, O, P |
| | Vesicular stomatitis virus (Indiana 2 and 3 subtypes) | H, B, CP, EQ, O, P |
| Togaviridae | Eastern equine encephalitis virus (EEE) | H, A, BT, EQ, P, R |
| | Rubella virus | H |
| | Venezuelan equine encephalitis virus (VEE) | H, A, EQ, R |
| | Spring viremia of carp | F |
| | Western equine encephalitis virus (WEE) | H, A, EQ |

A = avian;
B = bovine;
BT = bat;
C = canine;
CP = caprine;
CV = cervine;
EQ = equine;
F = feline;
FR = ferret;
H = human;
L = lagomorph;
R = rodent;
NHP = non-human primate;
O = ovine;
P = porcine The Examples below describe optimization of the methods disclosed herein. The Examples below are included to demonstrate particular embodiments of the disclosure. It should be appreciated by those of ordinary skill in the art that the techniques disclosed in the Examples represent techniques and compositions discovered by the inventors to function well in the practice of the disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the disclosure.

The Examples provide in vitro methods for testing compounds for RIG-I agonist and/or anti-viral activity of the disclosure. Other in vitro virus infection models that can be used include but are not limited to flaviviruses such as bovine diarrheal virus, West Nile Virus, and GBV-C virus, other RNA viruses such as respiratory syncytial virus, and the HCV replicon systems (32). Any appropriate cultured cell competent for viral replication can be utilized as antiviral assays.

Example 1

1A. Development of an HCV Viral Countermeasures Screening Cell Line to Identify RIG-I Agonists with Antiviral Properties Reporter U2OS cell lines were developed to stably express (i) the HCV countermeasure NS3/4A protease under control of tetracycline and (ii) Firefly luciferase utilizing the IFN-β promoter. The NS3/4A protease is expressed under the control of a Tetracycline-repressive promoter (i.e., it is not expressed in the presence of Tetracycline). These cell lines were responsive to stimuli that modulate the RIG-I pathway including, without limitation, Sendai virus infection as well as IFN treatment and were utilized to identify RIG-I modulators through high throughput screening (HTS)

of a small molecule library. Induction of reporter cell lines was optimized for cell growth and assay conditions used in the HTS, in order to obtain the most sensitive and reproducible results. Additionally, a control cell line that expresses *Renilla luciferase* using the β-actin promoter was developed as a negative control. The β-actin cell line was utilized in a counter screen to identify compounds that cause nonspecific changes in global gene expression.

1B. Cloning of IFN-β and β-Actin Promoter Constructs

β-actin promoter sequence was amplified from stock genomic DNA using the following primers:

```
                                       (SEQ ID NO: 9)
Actin 5' SacI:      GGGAGCTCCCCAAGGCGGCCAAC
and (SEQ ID NO: 10)
Actin 3' HindIII:   GGAAGCTTGGTCTCGGCGGTGGT.
```

The IFN-β promoter including the following sequence,

```
                                       (SEQ ID NO: 11)
CTAAAATGTAAATGACATAGGAAAACTGAAAGGGAGAAGTGAAAGTGGGA

AATTCCTCTGAATAGAGAGAGGACCATCTCATATAAATAGGCCATACCCA

TGGAGAAAGGACATTCTAACTGCAACCTTTCG,
``` was inserted into the pGL4.14 luciferase construct (available from Promega, Inc.) using SacI and HindIII restriction sites at the 5' and 3' ends respectively.

When necessary, the sequence fragments were amplified using Platinum PCR reactions. The PCR fragments were purified, digested with SacI and EcoRV or HindIII and ligated into the Promega luciferase vectors. The β-actin promoter sequence was ligated into the pGL4.76 vector which contains a hygromycin selectable marker. IFN-β promoter sequences were inserted into the pGL4.14 vector that contains a hygromycin selectable marker. Constructs were confirmed by sequencing and plasmid maps.

1C. Cells Expressing NS3/4a Viral Proteins

U2OS cells stably expressed the HCV NS3/4A gene encoding sequence (Genbank ID AY46460.1; SEQ ID NO: 1) under control of a Tetracycline-responsive promoter that repressed NS3/4A expression in the presence of Tetracycline.

1D. Production of Stable Cell Lines

U2OS cells that stably expressed the NS3/4A protease under control of the Tet-repressive promoter were seeded in a 6-well plate at $2.5 \times 10^5$ cells and grown overnight under normal growth conditions prior to transfection. Cells were transfected with 2 μg of the vector DNA using Lipofectin and Plus Reagent from Invitrogen according to the manufacturer's suggested reagent volumes and ratios. Following transfection, cells were grown to confluency (24-48 hours) and each well was then split into two 10 cm dishes. Cells were grown 24 hours and then media was replaced with selective media containing the appropriate antibiotic. The optimal concentration of antibiotics for U2OS cells was determined to be 400 μg/mL G418 and 250 μg/mL Hygromycin. Cells were grown in the presence of antibiotic until 80% of cells died under selective pressure and individual colonies appeared. When colonies contained >50 cells they were trypsinized from the plate, transferred to a 96-well plate and grown in the presence of antibiotic (only 20-40% of the clones survive this phase). Surviving clones were grown and passaged when they reached 80% confluency under normal conditions but with media containing antibiotic. All stable cell line clones were then tested for optimal induction of IFN-β in the presence of NS3/4A protease. In total, four stable clones were isolated for further testing.

1E. Luciferase Assays

Stable clones were grown under normal growth conditions and $1 \times 10^4$ cells in a volume of 100 μl of media were seeded in each well of an opaque-bottom 96-well dish (BD Bioscience) and grown to 80% confluence (usually 20 hours). Wells were treated in triplicate according to one of the following conditions: absence of Tetracycline (NS3/4A expression), absence of Tetracycline and infection with Sendai virus, presence of Tetracycline (NS3/4A repression), or presence of Tetracycline and infection with Sendai virus. After treatment, the cells were incubated at 37 degrees for an additional 18 hours. 50 μl of one-step luciferase reagent (Promega Steady-Glo) was added to each well and incubated at room temperature for 20 minutes, then read on a Berthold luminometer. Raw data was exported in matrix format to an Excel spreadsheet to be saved on the server.

1F. Reporter Cell Line Synthesis

U2OS cells (2A) that stably expressed the HCV NS3/4A protease under control of a Tet-repressive element were transiently transfected with reporter constructs containing the IFNβ promoter driving expression of firefly luciferase and tested for luciferase induction following Sendai virus infection. Luciferase induction was tested in two independent experiments done in triplicate wells to generate standard deviations. The 2A stable cell line was passaged and frozen in a cell bank for use in screening.

1G. Infection with Sendai Virus Causes Activation of IFNβ Expression

Figure 1:
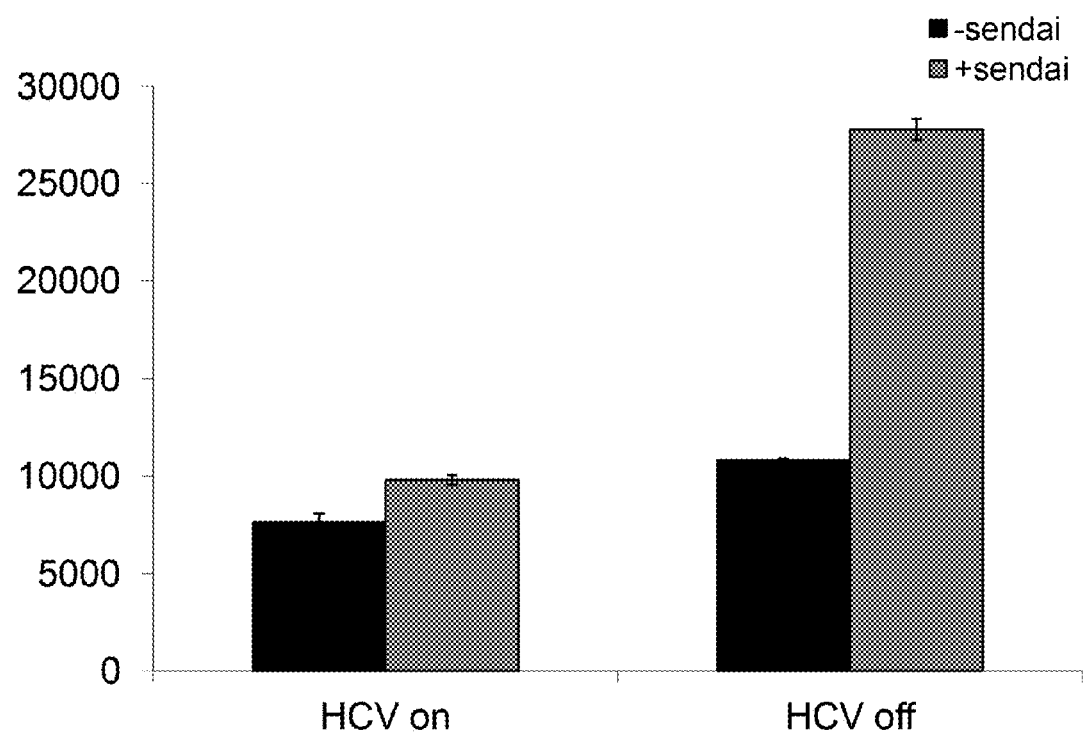
FIG. 1 shows induction of luciferase expression in clonally isolated NS3/4A cells that were stably transfected with a luciferase expression construct under control of the IFNβ Promoter, indicating activation of IFNβ expression after infection with Sendai virus (HCV on). In the presence of HCV NS3/4A protease, activation of IFN expression is abolished (HCV off).

Upon removal of Tetracycline and thus expression of NS3/4A, activation of IFNβ expression was abolished. IFNβ showed low basal levels of expression (no induction) that increased after Sendai infection only when NS3/4A was not expressed. When NS3/4A was expressed, there was no significant increase in expression over basal levels (FIG. 1). U2OS cell lines that contain both Tet-regulated NS3/4A protease and an integrated copy of the IFNβ-luciferase reporter construct were clonally isolated and tested for luciferase expression when infected with Sendai virus.

1H. Regulation of NS3/4a Expression by Tetracycline

Figure 2:
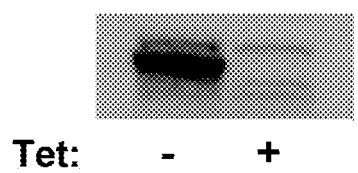
FIG. 2 shows expression of HCV NS3/4A protease in U2OS cells that stably express a construct with the NS3/4A gene under control of a Tetracycline-repressive promoter element. In the absence of Tet (left), NS3/4A is expressed at high levels; in the presence of Tet (right), NS3/4A expression is repressed.

Cells from clone 2A were plated in the absence or presence of Tetracycline. After 24 hours cells were harvested and lysed for protein. Western blot analysis of NS3/4A protein expression in the samples confirmed that in the absence of Tetracycline, NS3/4A protein was present in high levels; in the presence of Tetracycline, there was no NS3/4A protein expression (FIG. 2).

Figure 3:
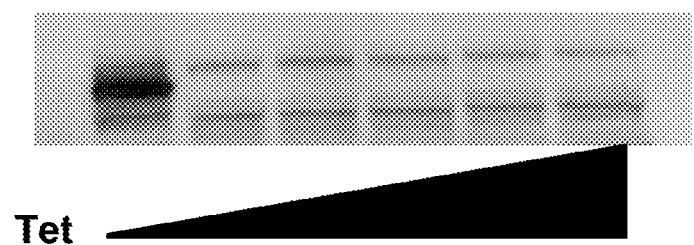
FIG. 3 shows titration of Tetracycline from left to right: no Tet, 12.5%, 25%, 50%, 75%, and 100% of normal concentration used in NS3/4A IFNβ cell culture. The minimal presence of Tet is sufficient to suppress HCV NS3/4A expression.

The final concentration of Tetracycline in culture was titrated down in order to determine whether protein levels of NS3/4A would be similarly titrated. Apparently NS3/4A was only expressed when Tetracycline was completely absent from the cell culture, because in the presence of even a minimal concentration of Tetracycline (12.5% of normal culture conditions) NS3/4A expression was abolished (FIG. 3).

1I. Optimization of Assay Conditions

Figure 4A:
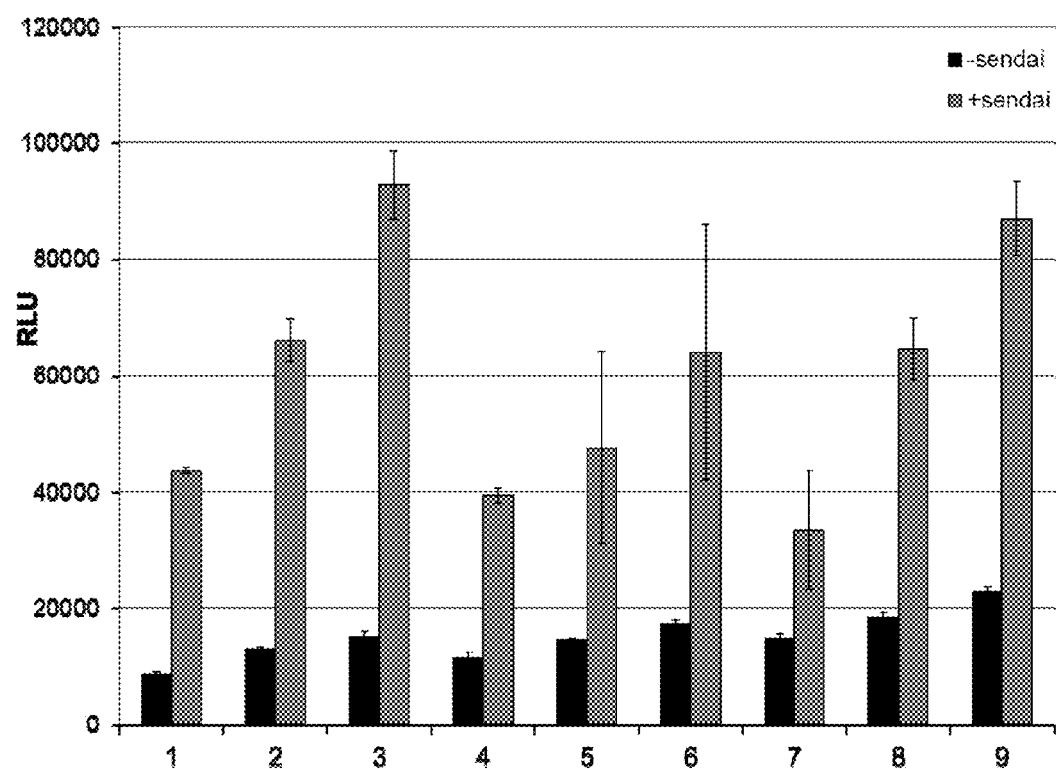
FIG. 4 shows induction of luciferase expression in NS3/4A IFNβ clone 2A cells under varying assay conditions. Both RLU (A) and fold induction (B) are shown.
Figure 4B:
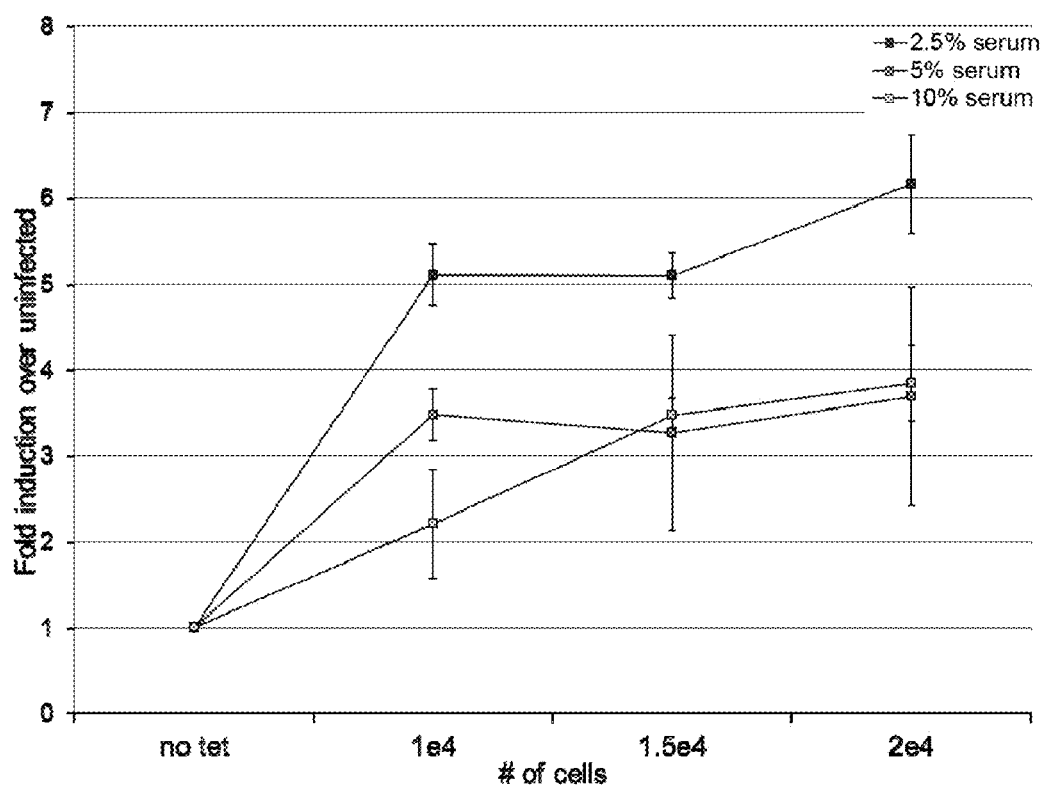

The growth and assay parameters were tested to identify the optimal conditions for conducting the high throughput screen in the NS3/4A IFNβ A cell line. Table 4 shows the assay parameters tested and the optimal conditions that were determined through detection of luciferase expression. The levels of induction following Sendai infection were used to analyze each parameter and the conditions giving the highest level of induction were chosen as optimal for screening purposes (FIG. 4).

TABLE 4

NS3/4A-IFNβ-Luc high-throughput screen optimization studies

| Assay parameter | Evaluated range | Optimized assay condition |
| --- | --- | --- |
| DMSO tolerance | 0.5-5% | 0.5% |
| Serum concentration | 0-10% | 2.5% |
| Cell plating density (96-well plates) | 5,000-20,000 cells/well | 10,000 |
| Positive controls | 0.5-200 HA/mL Sendai virus | 100 HA/mL Sendai |
| Endpoint reagent concentration | 25-200% | 50% |
| Luciferase reading conditions | Incubation and read time | 20 minutes, 1 sec |
| Reproducibility | n = 3 replicate plates on each of 3 days | n = 3 replicate plates on each of 3 days |

In summary, in this Example a stable cell line expressing both the HCV NS3/4A viral protease and firefly luciferase using the endogenous IFNβ promoter was chosen for identifying RIG-I agonists that acted in the presence of a viral countermeasure in the HTS. This cell line exhibited low levels of endogenous expression (background in the cell based screen) and high levels of induction (12 fold) following Sendai virus infection. Negative regulation of HCV NS3/4A viral protease expression by Tetracycline was very effective, with even a minimal amount of drug present being sufficient to repress expression. Two stable cell lines expressing *renilla luciferase* using the actin promoter were selected for low levels of basal expression and no response to Sendai or IFN exposure. Both actin cell lines can be further characterized for their response to agents that globally increase transcription levels. To optimize the assay parameters for carrying out the HTS, various conditions affecting cell growth and IFN induction were tested. The optimal concentration of cells, serum, DMSO, positive controls (Sendai in the presence of Tet) and luciferase substrate were determined. These conditions were utilized to screen a small molecule library for diverse modulators of the RIG-I pathway.

Example 2

Biological Activity of Identified Compounds

Figure 5A:
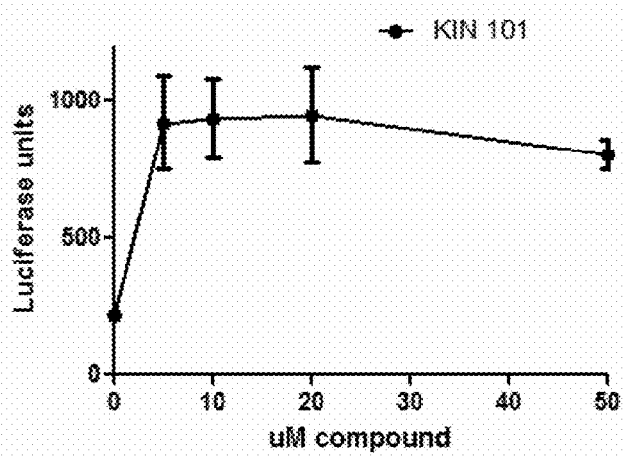
FIGS. 5A-5C show that a compound identified by the methods disclosed herein, KIN101, shows dose dependent ISG54 promoter induction and no effect on the actin promoter or cell growth.
Figure 5B:
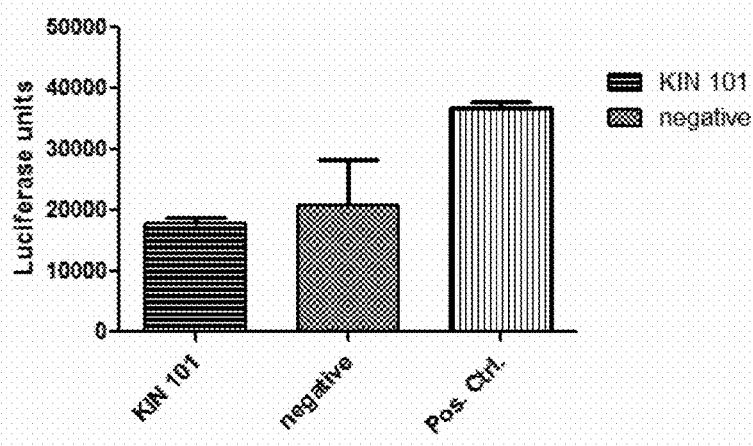
Figure 5C:
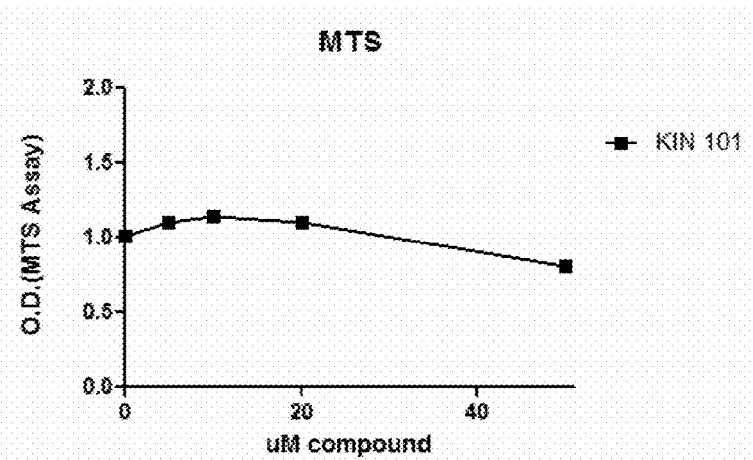

2A. Dose-Dependent ISG54 Promoter Induction by Isoflavone Compounds without Effect on the Actin Promoter or Cell Growth A compound referred to herein as "KIN101" was identified by the screening methods disclosed herein as a RIG-I modulator. Huh 7 cells stably expressing a luciferase cistron driven by the ISG54 promoter were treated with KIN101 for 18 hours and then analyzed for luciferase production. FIG. 5A shows a dose dependent increase in luciferase expression under control of the ISG54 promoter following exposure to KIN101.

Huh 7 cells expressing a luciferase construct driven by the actin promoter were treated with 10 uM of KIN101 and then analyzed for luciferase production. Negative control cells are treated with vehicle alone. KIN101 did not increase expression of luciferase under control of the actin promoter.

To assess a potential effect of KIN101 on cellular metabolism, Huh7 cells were grown for 48 hours with increasing doses of KIN101 and analyzed using an MTS assay (the higher the O.D. the more metabolism occurring). KIN101 did not affect cellular metabolism.

2B. Flu Data

MRC5 cells were pre-treated with increasing doses of KIN101 for 8 hours, infected with Influenza A virus WSN strain MOI=1.0 and grown for 24 hours. See FIG. 6A. Infected cells were detected using an ELISA method against the Influenza NP protein. Infected cells with no drug treatment were utilized as a positive control for infection.

Figure 6A:
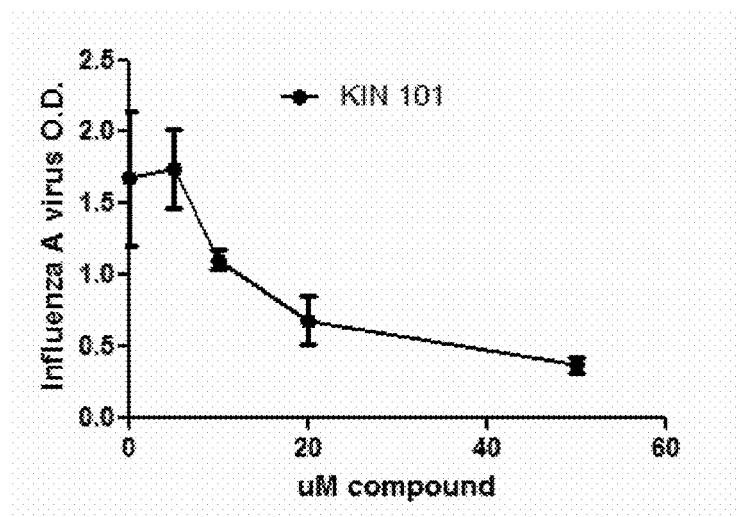
FIGS. 6A and 6B show data related to KIN101 and Influenza A.
Figure 6B:
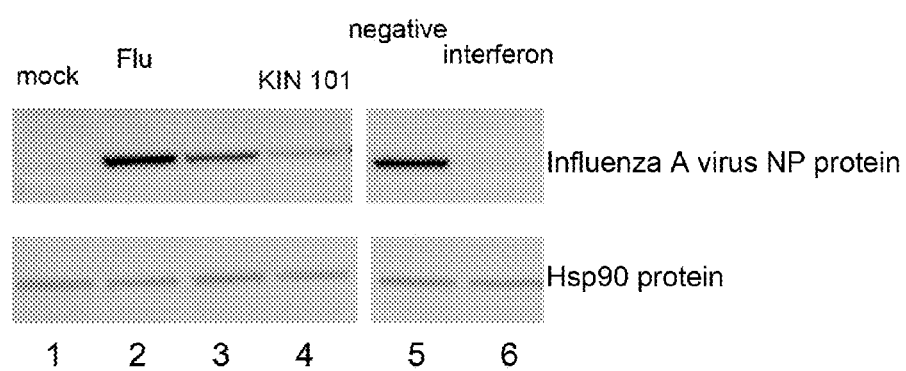

MRC5 cells were treated and infected as described for FIG. 6A. See FIG. 6B. 24 hours following infection cells were harvested, lysed and whole cell protein lysates were analyzed by western blot for Influenza NP protein. Mock infected cells were used to determine nonspecific background, and Flu infected cells with no drug treatment served as a positive control for infection and detection. Cells were treated with 10 μM KIN101 or 10 μM of a negative control compound, which was a compound showing no activity in screening assays for compounds with RIG-I modulator activity. Interferon was used a positive control for Flu infection inhibition. The bottom panel of FIG. 6B shows staining with Hsp90 as a loading control.

Figure 7A:
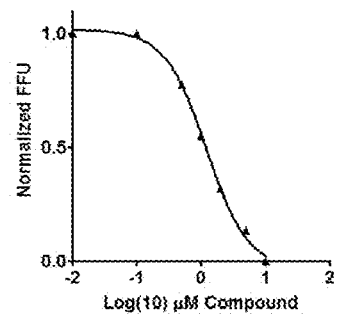
FIGS. 7A-7C show KIN101 activity against HCV-2a virus in cell culture methods.

2C. Isoflavone Activity Against HCV-2A and Influenza a Virus in Cell Culture Methods Huh 7 cells were treated with KIN101 for 24 hours and then infected with HCV-2a MOI=1.0. See FIG. 7A. Cells were grown for an additional 48 hours and then stained for HCV proteins. The number of infected cells versus concentration of KIN101 added was plotted in panel A.

Figure 7B:
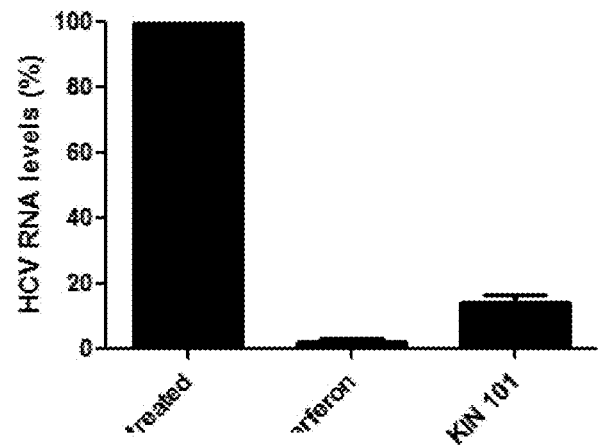

Huh 7 cells were pre-treated with KIN101 at 10 uM and grown for 18 hours. See FIG. 7B. Cells were then infected with HCV-2a MOI=1.0 and grown for an additional 72 hours. Supernatants from infected cells were harvested, HCV RNA was purified and viral RNA quantitated utilizing Real Time PCR with HCV specific primers. Cells infected with HCV that were not KIN101-treated were utilized as a control and values set to 100% infection rate. Interferon-alpha was used as a positive control for HCV inhibition.

Figure 7C:
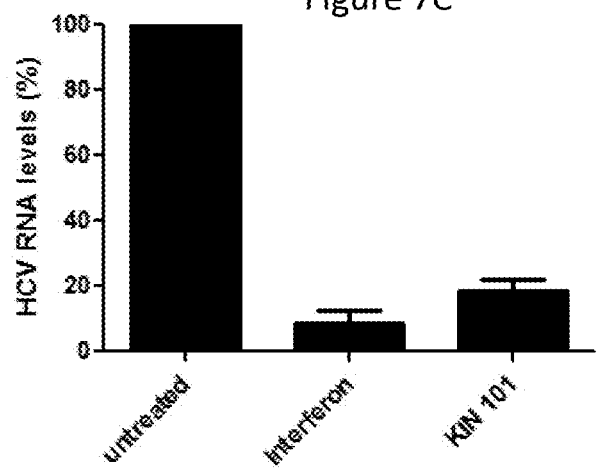

Huh 7 cells were infected with HCV-2a MOI=1.0 and 4 hours following infection compounds or interferon were added to infected cells. See FIG. 7C. The remainder of experiment was performed as described for FIG. 7B.

Figure 8A:
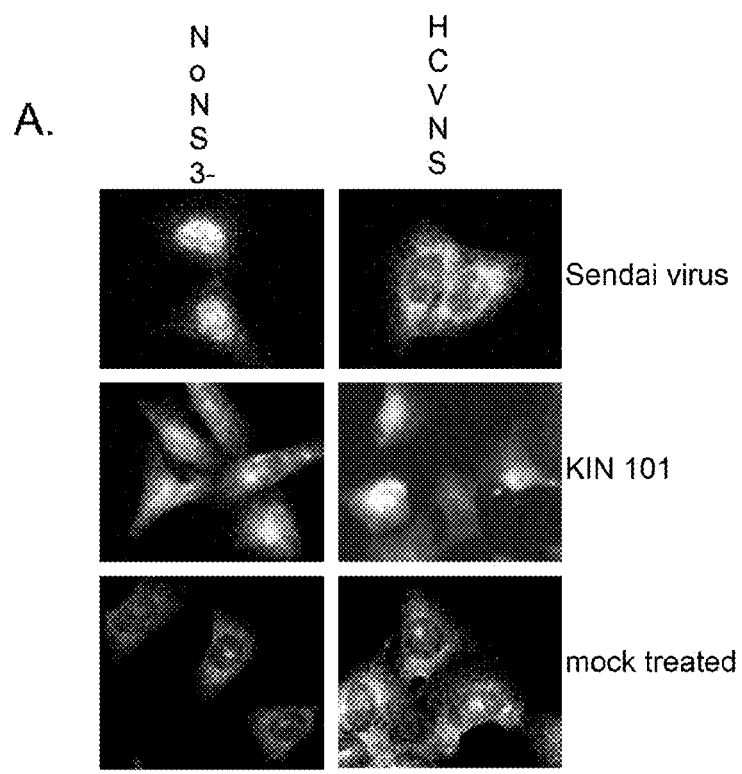
FIGS. 8A and 8B show KIN101 activates IRF-3 nuclear translocation in cells expressing HCV NS3 protease.
Figure 8B:
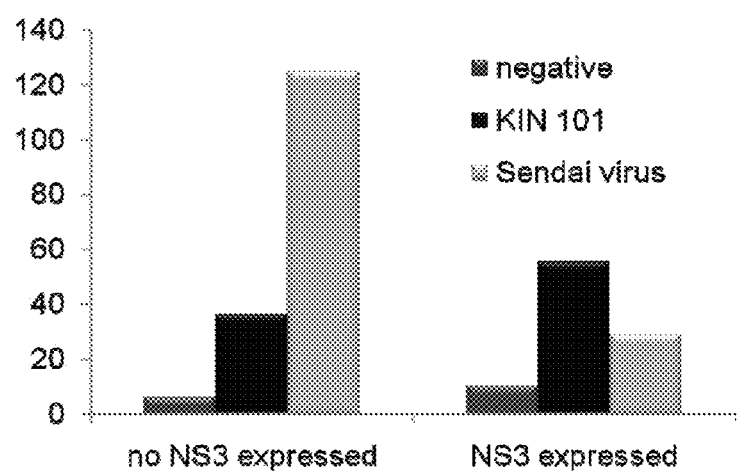

2D. Activation of IRF-3 Nuclear Translocation by KIN101 in Cells Expressing HCV NS3 Protease Human osteosarcoma cells were stably transformed with the HCV NS3-4A protease coding sequence under control of a tetracycline inducible promoter. See FIGS. 8A and 8B.

Cells were grown in the presence of tetracycline to keep expression of HCV protease off. Cells were grown with or without tetracycline and treated with KIN101 (10 uM) or controls for 18 hours. Cells were stained for IRF-3 and representative images are shown in the FIGs. Sendai virus infection was used as a control for IRF-3 translocation that was inhibited by HCV NS3-4A protease. Mock-treated cells were grown in media containing 0.5% DMSO. Images were analyzed on an Array Scan VTI to quantitate the IRF-3 staining in the nucleus and cytoplasm. Values shown demonstrate IRF-3 intensity in the nucleus.

Example 3

Antiviral Activity of Identified Compounds

To further characterize the breadth of antiviral activity of optimized molecules, cell culture infection models are used to analyze different HCV genotypes and influenza virus strains. In addition, optimized compounds are tested for activity against West Nile virus (WNV), an emerging public health concern. The studies include treating cells with compound 2-12 h. prior to infection or treating cells 8 h. after infection (see Table 6). Virus production and cellular ISG expression are assessed over a time course to analyze antiviral effects of representative compounds from lead structural classes. IFNβ treatment is used as a positive control.

Virus production is measured by focus-forming or plaque assay. Huh 7 cells are pre-treated with compound for 24 hours and infected with HCV2a at an MOI of 0.5 for 48 hours. HCV proteins are detected by immunofluorescent staining with viral-specific serum and foci normalized to negative control cells that are not drug treated (equal to 1).

In parallel experiments, viral RNA and cellular ISG expression are measured by qPCR and immunoblot analyses. These experiments are designed to validate compound signaling actions during virus infection, and assess compound actions to direct innate immune antiviral programs against various strains of viruses and in the setting of virus countermeasures. Detailed dose-response analyses of each compound are conducted in each virus infection system to determine the effective dose that suppresses virus production by 50% (1050) and 90% (1090) as compared with control cells for both the pre-treatment and post-treatment infection models.

TABLE 6

Virus systems and study design for antiviral analysis of lead compounds

| Virus | Virus Strain | Study Design |
|---|---|---|
| HCV | H77 (genotype 1a) | Assays |
| | JFH1 (genotype 2a) | Plaque or focus forming |
| FLU | High pathogenicity in mice | assays (infectious virus) |
| | A/PR/8/34 (H1N1 mouse-adapted virus) | qPCR (RNA levels) |
| | A/WSN/33(H1N1 mouse-adapted neurovirulent virus) | Immunoblot and ELISA (protein levels) |
| | Low pathogenicity in mice | Study Design |
| | A/Texas/36/91 (H1N1 circulating virus) A/Udorn/72 (H3N2) | Compound treatment of cells pre- and post-infection |
| WNV | TX02 (lineage 1) MAD78 (lineage 2) | Determine $EC_{50}$ and $EC_{90}$ Inhibition of viral life cycle |

Example 4

4A. In Vivo Pharmacokinetic, Toxicological, and Antiviral Properties of Optimized Identified Compounds in Preclinical Animal Models Preclinical Pharmacokinetic and Tolerability Profiling The in vivo pharmacokinetic (PK) profile and tolerability/toxicity of Identified compounds are evaluated in order to conduct further characterization of their antiviral activity in animal models of influenza virus and WNV infection. Mouse is the chosen test species for these studies since it is the most commonly used rodent model of WNV and influenza.

A reverse-phase, HPLC-MS/MS detection method is used for measuring the concentration of each compound in mouse plasma. Prior to PK profiling, an initial oral and intravenous formulation for each compound is developed using a limited formulation component screen that is largely focused on maximizing aqueous solubility and stability over a small number of storage conditions. Existing analytical methods known in the art are used to measure formulation performance. A formulation is developed for each compound following a three tiered strategy:

Tier 1: pH (pH 3 to 9), buffer, and osmolality adjustment;
Tier 2: addition of ethanol (<10%), propylene glycol (<40%), or polyethylene glycol (PEG) 300 or 400 (<60%) co-solvents to enhance solubility;
Tier 3: addition of N—N-dimethylacetamide (DMA, <30%), N-methyl-2-pyrrolidone (NMP, <20%), and/or dimethyl sulfoxide (DMSO, <20%) co-solvents or the cyclodextrins (<40%) as needed to further improve solubility.

For selected identified compounds that demonstrate adequate performance in in vitro antiviral, mechanistic, ADME, and toxicology studies, a preliminary mouse PK study is performed (see Table 7). Each compound is administered as a single dose to animals by oral gavage (<10 ml/kg) or i.v. bolus injection (<5 ml/kg) after an overnight fast. Multiple animals are dosed for each dosing group such that 3 animals are sampled at each time point. Blood samples are collected by retro-orbital sinus prior to dosing and at 5, 15, and 30 min., and 1, 2, 4, 8, and 24 h. post-dosing. Drug concentrations are measured according to the previously developed bioanalytical methods. Pharmacokinetic parameters are evaluated using the WinNonlin software.

TABLE 7

| Study | Experimental design | Route of administration | Outcomes |
|---|---|---|---|
| Mouse PK | Single dose pharmacokinetic study | IV and Oral | Oral bioavailability, $C_{max}$, $t_{1/2}$, Cl, $V_d$, $AUC_{0-24, 0-\infty}$ |
| Mouse tolerability | Phase 1: ascending dose tolerability and MTD determination; Phase 2: placebo controlled 7-day toxicity at MTD | Oral | MTD, acute toxicity, hematology, serum chemistry, gross pathology |

Based upon their performance in exploratory PK studies, compounds are further evaluated for preliminary tolerability and toxicity in mice prior to their characterization in antiviral models. Tolerability studies are performed in two stages: an initial dose escalation stage (up to 5 doses, each separated by a 5-day washout period) to determine the maximum tolerable dose (MTD, Phase 1), followed by seven daily administrations of the MTD to evaluate acute toxicity (Stage 2) (see Table 8). All doses are administered by oral gavage. In an exemplary experiment, five animals of each sex are placed on-study in stage 1 and 15 animals per sex per dosing group in Stage 2. Study endpoints include a determination of the MTD, physical examination, clinical observations, hematology, serum chemistry and animal bodyweights. Gross pathology is performed on all animals whether found dead, euthanized in extremis, or at the intended conclusion of the experiment. The toxicology studies identify early toxicological endpoints, and drive selection of lead candidates for antiviral animal models.

TABLE 8

In vivo studies of compound actions against WNV and influenza virus

| Experiment | Analysis | Goal | Exemplary No. of Mice* |
|---|---|---|---|
| Effective compound dose determination | Viral burden analysis in serum | Define in vivo $EC_{50}$ and $EC_{90}$ | 238 |
| Viral pathogenesis study 1: $EC_{50}$ and $EC_{90}$ treatment | Time to moribund state, clinical scoring for pathologic signs of infection | Define compound action toward limiting viral pathogenesis | 739 |
| Viral pathogenesis study 2: $EC_{50}$ and $EC_{90}$ treatment and time course analysis | Viral burden analysis in serum and various target organs | Define compound action toward limiting virus replication and spread | 1056 |
| Viral pathogenesis study 3: (neuroinvasion model) $EC_{50}$ and $EC_{90}$ treatment | Time to moribund state, clinical scoring for pathologic signs of infection | Define compound action toward limiting viral pathogenesis in the CNS | 370 |

*Numbers reflect an average of at least two iterations of each experiment

4B. Evaluation of Antiviral Properties and Immune Protection Using Mouse Infection Models Optimized compounds are selected based on compound pharmacokinetic, antiviral, and innate immune actions for further evaluation in preclinical mouse models of infection (Table 8). Innate immune actions of the compounds are measured, and their ability to protect mice from WNV and influenza virus challenge assessed. For the WNV infection model, subcutaneous footpad infection of wild-type C57BI/6 mice with the virulent lineage 1 strain of WNV (WNV-TX) is performed (29). Non-surgical tracheal instillation is performed for influenza virus strains NPR/8/34, A/WSN/33, and A/Udorn/72.

The influenza virus strains used for certain experiments are of two different subtypes (H1N1 and H3N2) and exhibit varying pathogenic properties and clinical presentations in C57BI/6 mice (30). Mice are monitored for morbidity and mortality over a range of challenge doses (such as, 10 to 1,000 pfu of virus) either alone or in combination with compound treatment beginning 12 h. before or 24 h. after infection and continuing daily subject to the determined plasma half-life of the drug. Compound dose-response analysis and infection time course studies are conducted to evaluate compound efficacy to: 1) limit serum viral load, 2) limit virus replication and spread in target organs, and 3) protect against viral pathogenesis.

For WNV, in addition to serum, viral burden is assessed in lymph nodes, spleen, and brain; for influenza virus, viral burden is assessed in heart, lung, kidney, liver, and brain. Incorporated in the design of these experiments is the determination of an effective dose for 50% and 90% suppression of serum viral load (ED50 and ED90) by each compound after a standard challenge of 100 pfu of WNV-TX or 1,000 pfu of influenza virus. Serum viral loads are determined by qPCR of viral RNA at 24 h. intervals following compound treatment. The compound actions are tested at the ED50 and ED90 toward limiting WNV pathogenesis in the cerebral nervous system using a WNV neuroinvasion model of infection (31).

Mice are monitored for morbidity and mortality after standard intracranial challenge of 1 pfu of WNV-MAD, either alone or in combination with compound treatment beginning 24 h. after infection.

Example 5

Methods to Identify Small Molecules that Induce RIG-I Gene Promoters

5A. Development of Screening Cell Line

Huh 7 cells were stably transfected with a luciferase promoter construct driven by the consensus ISG54 promoter. The following sequence was inserted into the pGL4.17 construct (Promega) using the restriction sites indicated (underlined):

(SEQ ID NO: 12)

GAGCTCCTCCGGAGGAAAAAGAGTCCTCTAAAGTATAATAAAAAGAAAAA

AAGAAAAAGAGTCCTGCCAATTTCACTTTCTAGTTTCACTTTCCCTTTTG

TAACGTCAGCTGAAGGGAAACAAACAAAAAGGAACCAGAGGCCACTTGTA

TATATAGGTCTCTTCAGCATTTATTGGTGGCAGAAGAGGAAGATTTCTGA

AGAGTGCAGCTGCGATATC.

Huh 7 cells were transfected with plasmid DNA and grown under G418 selection until resistant clones were isolated and tested for luciferase expression. The B-actin cell line was created in similar manner; the actin promoter sequence below was inserted into the pGL4.76 vector (Promega):

(SEQ ID NO: 13)

GAGCTCCCCAAGGCGGCCAACGCCAAAACTCTCCCTCCTCCTCTTCCTCA

ATCTCGCTCTCGCTCTTTTTTTTTTTCGCAAAAGGAGGGGAGAGGGGGTA

AAAAAATGCTGCACTGTGCGGCGAAGCCGGTGAGTGAGCGGCGCGGGGCC

AATCAGCGTGCGCCGTTCCGAAAGTTGCCTTTTATGGCTCGAGCGGCCGC

GGCGGCGCCCTATAAAACCCAGCGGCGCGACGCGCCACCACCGCCGAGAC

CAAGCTT.

Huh 7 cells were transfected with plasmid DNA and grown under hygromycin selection unto resistant clones were isolated. The diversity library contained 20,000 small molecules from Life Chemicals that fulfill the requirements for drug-like properties (Lipinski's rule of five). Molecules were selected to maintain maximal structural diversity in the library.

5B. High-Throughput Screening Assay

Reporter cell lines were cultured under antibiotic selection until seeding. Cells were seeded in white opaque bottom 96-well tissue culture plates at a density of 1×10$^4$ cells/well and grown for 24 hours without antibiotic selection. Each assay plate had wells A1, B1, C1, and D1 treated with DMSO only to a final concentration of 0.5%; wells E1, F1, G1, and H1 were infected with 10 HA Sendai virus as a positive control for ISG54-driven luciferase induction. The remainder of the wells were treated with compound diluted to a final concentration of 10 µM in media containing 0.5% DMSO. Cells were incubated with control or compound treatment for 24 hours. Steady-Glo luciferase reagent (Promega) was added at 50 µL per well, mixed thoroughly, and incubated at room temperature for 20 minutes. Luminescence was quantitated per well using a luminometer (Berthold). Confirmation of initial hits was performed in triplicate.

5C. MTS Assay as a Measure of Cytotoxicity

Figure 9:
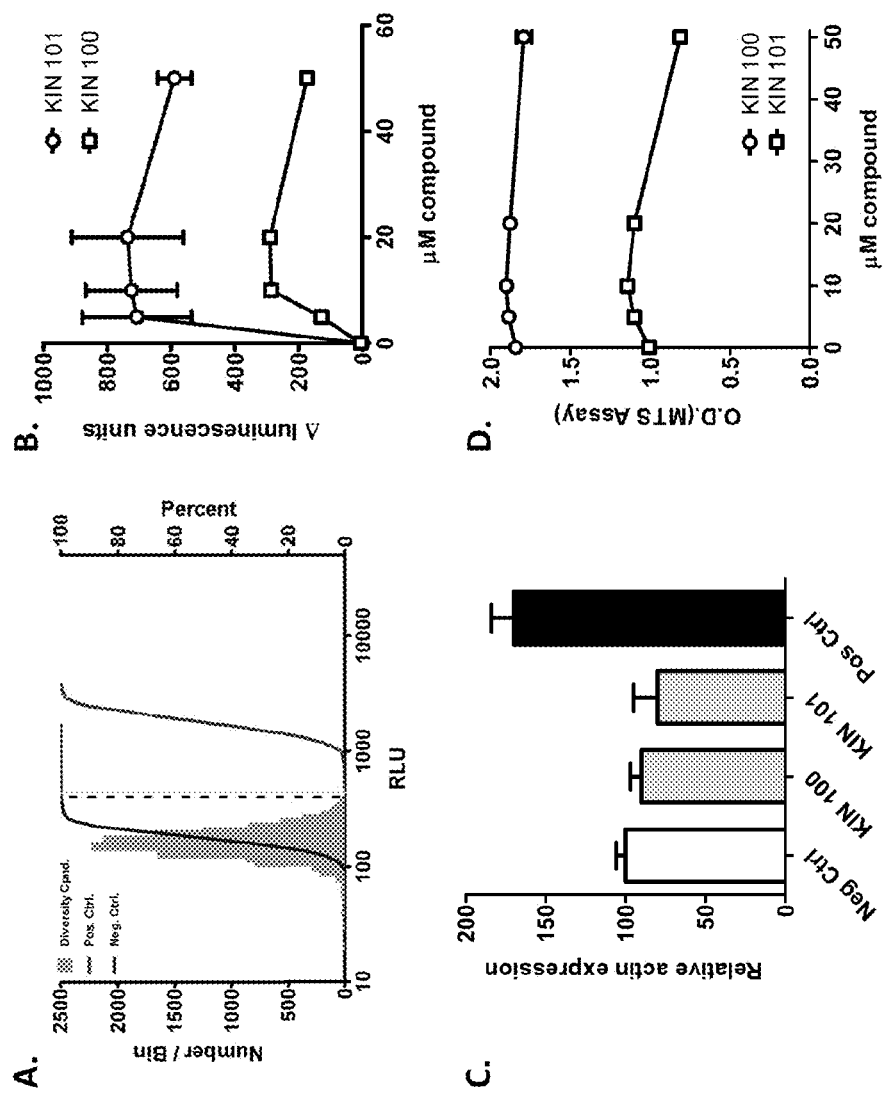
FIG. 9 shows identification of the small molecules KIN100 and KIN101 from a high-throughput screen for RIG-I agonist activity. A 20,000-member diversity library was screened at 10 μM to identify compounds that induced ISG54 luciferase reporter activity. Uninfected cells (negative control) and Sendai virus infected cells (positive control) are represented on the histogram along with the sample population. The four standard deviation threshold that was used to identify positive hits is indicated by the vertical dashed line (A). Huh7 cells stably expressing a luciferase reporter gene driven by the ISG54 promoter were treated with compound for 18 h and showed dose dependent luciferase production (B). Huh7 cells expressing a luciferase construct driven by the actin promoter were treated with 10 μM of compound and then analyzed for luciferase production. Negative control cells were treated with vehicle alone (0.5% DMSO). Positive control cells were treated with a compound from the diversity library that showed reproducible activation of the actin promoter (C). Huh7 cells were grown for 48 h with increasing doses of compound and analyzed using an MTS assay to measure cellular metabolism (the higher the O.D. the higher the metabolic activity) (D).

Huh 7 cells were seeded in clear bottom 96-well tissue culture plates and grown for 24 hours. Seeded cells were treated with increasing concentrations of compound (0, 5, 10, 20, and 50 µM in media containing 0.5% DMSO) for 24 hours. Negative control wells contained 0.5% DMSO only and positive control for cytotoxicity was examined using an EMCV infection which causes 100% cytopathic effect. The proportion of viable cells was calculated using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; MTS] to a colored formazan compound in live cells. The conversion of MTS to formazan was detected by a 96-well microtiter plate reader, and the resulting optical densities (O.D.) were used directly to estimate cell viability. Cells were incubated for three hours in the presence of one-step reagent (Cell Titer One, Promega) before O.D. reading was done. Experiments were performed in triplicate. Identification of KIN100 and KIN101 as hits from the screen described in this Example is shown in FIG. 9.

Example 6

Methods to Identify Antiviral Activity of KIN101

6A. HCV Immunofluorescent-Based Antiviral Assay

Huh 7 cells were seeded as described above for the IRF-3 immunofluorescent assay. Cells were treated with 10 µM compound in media containing 0.5% DMSO. After 24 hours the media solution with compound was removed temporarily from wells. The cells were washed with PBS before HCV2a virus was added at the stated MOI. Virus was incubated for 2-4 hours and then removed. The cells were washed with PBS and the compound solutions were replaced into each well. The cells were grown overnight and then monolayers were fixed and stained for HCV proteins. Primary serum PHS#72 was used (1:3000). Secondary anti-human antibody conjugated to Dylight 488 or Alexa 488 (FITC equivalent) and Hoescht dye (nuclear stain) were used for detection of HCV protein and cell nuclei. Following secondary antibody incubation the monolayers were washed and left in 100 µL wash buffer for imaging as described above. The number of infected cells was quantitated based on positive staining. Compound treatments were done in triplicate.

6B. Real-Time Quantitative PCR (qPCR) to Measure HCV RNA

Huh 7 cells were seeded and treated as described above for the HCV antiviral assay. Alternatively, the compound was added post-infection, 6 hours after HCV was added. The cells were infected as described above at MOI greater than or equal to 1.0. 72 hours post-infection the viral RNA was purified from culture media using the Qiagen Viral Amp kit as manufacturer directed. The genome copies of HCV2a in 5 µL of RNA purified from supernatants was quantitated by qPCR. To create a standard curve for HCV RNA, in vitro transcribed HCV2a was serially diluted from $10^1$-$10^{12}$ in nuclease free water and 5 µL was added to the master mixture of PCR reagents. HCV2a primers were optimized and the following primers were utilized:

5' GCACCATGAGCACAAATCCTAA 3'    (SEQ ID NO: 14)
and

5' GGAACTTAACGTCTTCTGGG 3'.    (SEQ ID NO: 15)

PCR was performed under the normal conditions for a 20 µL Power SYBR Green reaction (Applied Biosystems) with 125 nM of each HCV primer.

6C. Influenza a ELISA Antiviral Assay

A549 cells were seeded in a clear bottom 96-well tissue culture plate at a density of 1×104 cells/well and grown for 16 hours. Seeded cells were treated with increasing concentrations of compound (0, 5, 10, 20, and 50 µM in media containing 0.5% DMSO) for 6 hours and then infected with 250 pfu Influenza WSN strain. Diluted virus was added directly to the well and compound was not removed. Cells were grown for a total of 24 hours post compound treatment and fixed with methanol:acetone. Cells were blocked with horse serum and BSA in the presence of Triton X-100. Mouse anti-Influenza A nucleoprotein monoclonal antibody (Chemicon) was used (1:3000). Secondary anti-mouse IgG-HRP (Pierce) was used (1:3000). The reaction was developed using TMBK BioFX reagents as manufacturer suggested. Following reagent addition the cells were incubated at room temperature for 2-5 minutes and 2N HCl was used to stop the reaction. Plates were read at 450 nm on a microtiter plate reader.

6D. Western Blot to Measure Influenza a Virus Protein

Cells were grown, treated and infected as described above for the Influenza WSN ELISA assay. Alternatively, infected cells were harvested for protein lysates 24 hours post infection/treatment by washing the cells once with PBS and lysing the cells in RIPA buffer. Lysates were harvested and analyzed for proteins by western blot analysis with the same anti-Influenza antibody described above. The antiviral activity of KIN101 against HCV and Influenza A is demonstrated in FIG. 10.

Example 7

RIG-I Agonist Activity by KIN101

7A. Immunofluorescent Assay for Nuclear Translocation of IRF-3

Huh 7 cells were seeded in clear bottom 96-well tissue culture plates at a density of 5×10$^3$ cells per well and grown for 24 hours. Cells were treated with compounds at final concentrations of 20 µM and 10 µM in media containing 0.5% DMSO. Negative control cells contain 0.5% DMSO only and positive control cells were infected with 10 HA of Sendai virus. Cells were incubated for 24 hours and then monolayers were fixed in 4% paraformaldehyde, permeabilized and stained for IRF-3 protein. Staining was performed as directed by instructions in the Cellomics translocation kit (Thermo Scientific). Rabbit polyclonal antibody against IRF-3 was used (1:400). Secondary anti-rabbit antibody conjugated to Dylight 488 (FITC equivalent) and Hoescht dye (nuclear stain) were used for detection of cellular IRF-3 and cell nuclei. Following secondary antibody incubation the monolayers were washed and left in 100 µL wash buffer for imaging. IRF-3 (FITC) and nuclear staining (DAPI) were viewed and quantitated by inverted microscope. Images were taken using MetaMorph software and saved as high resolution image files. Compound treatments were done in triplicate.

7B. Immunofluorescent Assay for Nuclear Translocation of IRF-3 in Cells Expressing Viral Countermeasure U2OS NS3/4A cells were thoroughly washed to remove Tetracycline and then seeded for the assay in the absence of Tetracycline to enable NS3/4A expression. Compound treatments were done as described above for Huh 7 cells.

KIN101 induced nuclear translocation of IRF-3, indicating activation of the transcription factor and upregulation of RIG-I signaling, as shown in FIG. 11 and FIG. 12. KIN101 induced expression of discrete immune pathways centered on IRF signaling. Expression microarray analysis and bioinformatics were performed as follows. Total RNA isolation and mRNA amplification were performed on equal masses of total RNA from MRC5 cells treated with either DMSO, negative control, or 10 µM KIN101 at 20 hours post treatment, and from MRC5 cells infected with Sendai virus at 20 hours post infection.

Probe labeling and microarray slide hybridization were performed with the Agilent Whole Human Genome microarrays, wherein each microarray contains 44K probes, corresponding to approximately 41,000 human genes. Slides were scanned with an Agilent DNA microarray scanner, and the resulting images were analyzed using Agilent Feature Extractor (AFE) version 9.5.3.1. All data were entered into a custom-designed Oracle 9i-backed relational database (Labkey, Inc., Seattle, Wash.) and uploaded into Rosetta Resolver System 7.2 (Rosetta Biosoftware) and Spotfire Decision Site 9.1.1 (Spotfire AB) for analysis and visualization.

7C. Statistical Analysis

One-way analysis of variance (Textbook ANOVA, Benjamini-Hochberg multiple-test corrected P-value <0.01) was performed to determine gene expression differences across treatments (KIN101, negative control, and DMSO). Probes identified by ANOVA analysis were further filtered to include only those genes found to have significantly different expression compared to DMSO treatment (post-hoc test of ANOVA results, Scheffe P-value <0.1) that were also >2 fold different as compared with the expression from DMSO treated cells.

Functional analysis of statistically significant gene expression changes was performed with IPA® (Ingenuity Systems, Inc., Redwood City, Calif.). This software analyzes RNA expression data in the context of known biological response and regulatory networks as well as other higher-order response pathways. IPA functional analysis identified biological functions and/or diseases that were most significant among differentially regulated genes. In the functional networks, genes are represented as nodes, and the biological relationship between 2 nodes is represented as an edge (line). All edges are supported by at least 1 published reference or from canonical information stored in the Ingenuity Pathways Knowledge Base.

Quantitative real-time PCR was used to validate certain transcriptional changes found by microarray analysis. Primer and probe sets for each of the target sequences were chosen from the Applied Biosystems Assays-on-Demand product list. Assays were performed on an ABI 7500 Real Time PCR System using TaqMan chemistry.

Western blot was used to quantitate levels of IRF centric gene products in human whole cell lysates from cells treated with KIN101. Distinct gene expression of KIN101 treated human cells is shown in FIG. 12 and FIG. 13.

Example 8

KIN101 Causes a Discrete Upregulation of Innate Immune Pathways

Because multiple host pathways can contribute to ISG induction and antiviral activities, gene expression profiling was used to identify the pathways that are affected by KIN101 and to determine whether there might be broader non-specific gene expression changes that would be undesirable for an antiviral drug.

MRC5 cells were treated with KIN101 (10 µM) or a negative control (selected from the diversity library for having no activity in screening assays) for 20 h. Sendai virus infection was used as a positive control for the up-regulation of innate immune pathways. Total RNA was purified from triplicate samples to enable statistical analysis of the microarray data.

KIN101 treatment resulted in the differential expression of 75 genes (ANOVA p-value <0.01, >2 fold change between groups; 64 up-regulated, 11 down-regulated) compared to DMSO treatment alone. This was markedly more constrained than the number of genes perturbed by either IFN treatment or virus infection in this or previous studies (33). FIG. 15 shows the top 20 probes (corresponding to 18 genes) that were up-regulated following treatment with KIN101 compared with that seen in control cells treated with DMSO alone. The complete list of 75 genes is shown in FIG. 16. Gene expression patterns in cells that were treated with the negative control compound showed no significant difference from those observed in DMSO-treated cells, and cells infected with Sendai virus as a positive control demonstrated a significant up-regulation of innate immune pathways (FIG. 14).

Example 9

KIN 101 Inhibits RSV. 9A

HeLa cells were infected with RSV A2 strain MOI=1.0 and were then treated with KIN101 for 48 hours. Cells were grown under normal growth conditions and cell viability was determined by counting the number of live cells and comparing drug treated and RSV infected cells to infected cells that were mock treated (no drug; vehicle alone). Cells were stained with trypan blue and counted using a hemacytometer. The number of live cells versus concentration of KIN101 added was plotted. See FIG. 17A.

9B

HeLa cells were infected with RSV-A2 MOI=1.0 and subsequently treated with KIN101 at the indicated concentrations and grown for 48 hours. Supernatants from infected cells were harvested, RSV RNA was purified and viral RNA quantitated utilizing Real Time PCR with RSV specific primers. Cells infected with RSV that were not KIN101-treated were utilized as a control. See FIG. 17B.

9C

HeLa cells were seeded to 90% confluency and infected with RSV at MOI=1.0 (1^3 dilution) or MOI=0.1 (1^4 dilution) for 2 hours. Virus was removed and cells were overlayed with agar in the presence of KIN101 10 uM. Infected cells were incubated for 3-4 days to allow for RSV plaque formation. Plaques were visualized by staining with crystal violet. See FIG. 17C.

Example 9 data demonstrates that compounds identified by the described methods significantly inhibit RSV. KIN 101 protects cells from RSV induced cytopathic effects and cell death (FIG. 17A), decreases the amount of RSV viral RNA produced by infected cells (FIG. 17B) and decreases the number and size of viral induced plaques (FIG. 17C). These three examples show significant inhibition of RSV replication and cellular death caused by the virus. Drug inhibition of RSV shows that compounds identified by the methods disclosed herein inhibit paramyxoviruses.

Example 10

KIN 101 Inhibits Dengue Virus

HEK 293 cells were seeded to a confluency of 80% in a 6-well dish. Cells were grown for 18 hours under normal growth conditions. Cells were treated with the indicated concentration of KIN101 in media containing 0.5% DMSO for 18 hours. The next day drug was removed from treated cells and cells were infected with Dengue virus serotype 2 at an MOI=1.0; infected cells were incubated under normal growth conditions for 48 hours. For Dengue virus analysis whole cell lysates were prepared and analyzed by western blot for Dengue virus specific proteins. The amount of Dengue virus protein was quantitated and shown in FIG. 18.

Example 10 data demonstrates that compounds identified by the methods disclosed herein cause a potent and effective decrease in Dengue virus infection and growth. KIN101 causes a substantially complete inhibition of Dengue virus protein accumulation in cells infected with Dengue virus serotype 2 at 0.1 uM. This provides further evidence that the identified compounds inhibit different species of flaviviruses as shown by Hepatitis C virus and Dengue virus.

The following listing provides non-limiting embodiments of the present disclosure:

1. A method of treating a viral infection in a vertebrate by providing to said vertebrate a compound that modulates the activity of the RIG-I pathway in the presence of one or more viral countermeasures, wherein said compound is identified by a method comprising the steps of: (a) providing cells comprising a reporter gene under the control of a promoter in the presence of one or more viral countermeasures; (b) contacting said cells with putative RIG-I pathway modulating compounds; (c) measuring reporter gene expression; and (d) selecting a compound that activates reporter gene expression above a selected threshold in the presence of the one or more viral countermeasures.

2. The method of embodiment 1, wherein said viral infection is an infection by an RNA virus.
3. The method of embodiment 1, wherein said virus is human influenza virus (A, B or C), Hepatitis C virus, West Nile virus, SARS-coronavirus, poliovirus, rhinovirus, coxsackievirus, hepatitis A virus, foot and mouth disease virus, human parainfluenza viruses 1-4, human respiratory syncitial virus, Nipah virus, measles virus, Dengue virus, yellow fever virus, tick-borne encephalitis virus, Japanese encephalitis virus, or St. Louis encephalitis virus.
4. The method of embodiment 1, 2, or 3, wherein at least one additional anti-viral pharmaceutical agent is provided to said vertebrate.
5. The method of embodiment 4, wherein said additional pharmaceutical agent is provided as part of the same pharmaceutical composition as said compound or separately from said compound.
6. The method of embodiment 4 or 5, wherein said pharmaceutical agent is PEGinterferon α-2a, PEGinterferon α-2b, Ribavirin, Oseltamivir, Zanamivir, Amantadine, and/or Rimantadine.
7. The method of embodiment 1, 2, 3, 4, 5, or 6, wherein the selected threshold of step (d) is four standard deviations above control level.
8. The method of embodiment 1, 2, 3, 4, 5, 6, or 7, wherein, prior to step (a), said compound is structurally selected for predicted binding to the ligand-binding domain of RIG-I.
9. The method of embodiment 1, 2, 3, 4, 5, 6, 7 or 8, wherein said cells are U2OS cells, PH5CH8 cells, HeLa cells, Hep2 cells, MRC5 cells, A549 cells, or Huh 7 cells.
10. The method of embodiment 1, 2, 3, 4, 5, 6, 7, 8 or 9, wherein the identified compound has the structure:

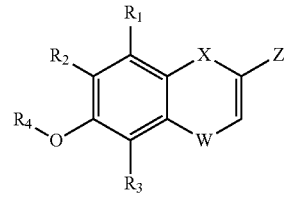

wherein $R_1$, $R_2$ and $R_3$ (independently) are H, lower alkyl, aryl, alkenyl, alkynyl, alkylaryl, arylalkyl, alkoxy, aryloxy, arylalkoxy, alkoxyalkylaryl, alkylamino, arylamino, heteroalkyl, heteroaryl, cyclic heteroalkyl, acyl, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, $SR_5$, $SOR_6$, $SO_2R_7$, $CO_2R_8$, $COR_9$, $CONR_{10}R_{11}$, $CSNR_{12}R_{13}$, $SO_nNR_{14}R_{15}$, $R_4$ (independently) is H, lower alkyl, aryl, alkenyl, alkynyl, alkylaryl, arylalkyl, alkoxyalkylaryl, alkylamino, arylamino, heteroalkyl, heteroaryl, cyclic heteroalkyl, acyl, alkylsulfonyl, arylsulfonyl and heterocyclicalkylalkyl, W is O or NH, X is C=O, S=O or $SO_2$, and Z is alkyl substituted alkyl, aryl, substituted aryl, heteroalkyl, heteroaryl, substituted heteroaryl, arylalkyl, heteroaryl alkyl.

11. The method of embodiment 1, 2, 3, 4, 5, 6, 7, 8, 9 or 10, wherein said viral countermeasure is NS3/4a, 3ABC, V protein, NS1, NS2, and/or VP35.
12. The method of embodiment 1, 2, 3, 4, 5, 6, 7, 8, 9, 10 or 11, wherein said vertebrate is a human, a bird, a dog, a cat, or a farm animal.

13. The method of embodiment 1, 2, 3, 4, 5, 6, 7, 8, 9, 10, 11 or 12, wherein said reporter gene is luciferase.

14. A method of identifying a compound that modulates the activity of the RIG-I pathway in the presence of one or more viral countermeasures, comprising the steps of: (a) providing cells comprising a reporter gene under the control of a promoter in the presence of one or more viral countermeasures; (b) contacting said cells with putative RIG-I pathway modulating compounds; (c) measuring reporter gene expression; and (d) selecting a compound that activates reporter gene expression above a selected threshold in the presence of the one or more viral countermeasures.

15. The method of embodiment 14, wherein the selected threshold of step (d) is four standard deviations above control level.

16. The method of embodiment 14 or 15, wherein, prior to step (a), said compound is structurally selected for predicted binding to the ligand-binding domain of RIG-I.

17. The method of embodiment 14, 15, or 16, wherein said cells are U2OS cells, PH5CH8 cells, HeLa cells, Hep2 cells, MRC5 cells, A549 cells, or Huh 7 cells.

18. The method of embodiment 14, 15, 16 or 17, wherein the identified compound has the structure:

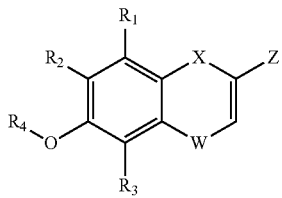

wherein $R_1$, $R_2$ and $R_3$ (independently) are H, lower alkyl, aryl, alkenyl, alkynyl, alkylaryl, arylalkyl, alkoxy, aryloxy, arylalkoxy, alkoxyalkylaryl, alkylamino, arylamino, heteroalkyl, heteroaryl, cyclic heteroalkyl, acyl, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, $SR_5$, $SOR_6$, $SO_2R_7$, $CO_2R_8$, $COR_9$, $CONR_{10}R_{11}$, $CSNR_{12}R_{13}$, $SO_nNR_{14}R_{15}$, $R_4$ (independently) is H, lower alkyl, aryl, alkenyl, alkynyl, alkylaryl, arylalkyl, alkoxyalkylaryl, alkylamino, arylamino, heteroalkyl, heteroaryl, cyclic heteroalkyl, acyl, alkylsulfonyl, arylsulfonyl and heterocyclicalkylalkyl, W is O or NH, X is C=O, S=O or $SO_2$, and Z is alkyl substituted alkyl, aryl, substituted aryl, heteroalkyl, heteroaryl, substituted heteroaryl, arylalkyl, heteroaryl alkyl.

19. The method of embodiment 14, 15, 16, 17 or 18, wherein said viral countermeasure is NS3/4a, 3ABC, V protein, NS1, N52, and/or VP35.

20. A cell used in a method of any of embodiments 1-19 above.

21. A cell that expresses luciferase under the control of a promoter and a viral countermeasure under the control of a Tet-repressive element in response to exposure to Sendai virus.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

REFERENCES

1. Tan et al. (2007) *Nat Biotechnol* 25, 1383-1389.
2. Lee et al. (2006) *Proc Natl Acad Sci USA* 103, 1828-1833.
3. Horsmans et al. (2005) *Hepatology* 42, 724-731.
4. Johnson et al. (2006) *Trends Immunol* 27, 1-4.
5. Li et al. (2005) *J Biol Chem* 280, 16739-16747.
6. Loo et al. (2008) *J Virol* 82, 335-345.
7. Loo et al. (2006) *Proc Natl Acad Sci USA* 103, 6001-6006.
8. Saito et al. (2007) *Proc Natl Acad Sci USA* 104, 582-587.
9. Saito et al. (2008) *Nature* 454, 523-527.
10. Sumpter et al. (2005) *J Virol* 79, 2689-2699.
11. Yoneyama (2004) *Nat Immunol* 5, 730-737.
12. Kawai et al. (2005) *Nat Immunol* 6, 981-988.
13. Meylan et al. (2005) *Nature* 437, 1167-1172.
14. Seth et al. (2005) *Cell* 122, 669-682.
15. Xu et al. (2005) *Mol Cell* 19, 727-740.
16. Venkataraman et al. (2007) *J Immunol* 178, 6444-6455.
17. Lipinski et al. (2001) *Adv Drug Deliv Rev* 46, 3-26.
18. Banerjee et al. (2008) *Cancer Lett* 269, 226-242.
19. Odaka et al. (1997) *J Biochem* 122, 116-121.
20. Philo et al. (1996) *J Biol Chem* 271, 6895-6902.
21. Philo (1996) *Biochemistry* 35, 1681-1691.
22. Kato et al. (2006) *Nature* 441, 101-105.
23. Yoneyama et al. (2005) *J Immunol* 175, 2851-2858.
24. Lescuyer et al. (2003) *Proteomics* 3, 157-167.
25. Taylor et al. (2003) *Nat Biotechnol* 21, 281-286.
26. Lutfalla et al. (1995) *EMBO J.* 14, 5100-5108.
27. Zou et al. (2009) *BMC Evol Biol* 9, 85.
28. Renard et al. (2001) *Nucleic Acids Res* 29, E21.
29. Suthar (2010) *PLoS Pathog* 6, e1000757.
30. Barnard (2009) *Antiviral Res* 82, A110-122.
31. Daffis et al. (2008) *J Virol* 82, 10349-10358.
32. Blight et al. (2002) J. Virology 76:13001-13014.
33. Cilloniz et al. (2010) J. Virology 84:7613-7624.

The invention claimed is:

1. A method of modulating innate immune signaling in the presence of viral countermeasures in a vertebrate, the method comprising:
identifying at least one compound that modulates activity of the RIG-I pathway in the presence of one or more viral countermeasures, wherein the at least one compound is identified by:
(a) providing cells comprising a reporter gene under the control of a promoter, wherein the one or more viral countermeasures are present in the cells and the one or more viral countermeasures are stably expressed in the cells;
(b) contacting the cells with putative RIG-I pathway modulating compounds;
(c) measuring reporter gene expression; and
(d) selecting a compound from among the putative RIG-I pathway modulating compounds that activates reporter gene expression above a selected threshold in the presence of the one or more viral countermeasures, and
administering the at least one compound to the vertebrate infected by influenza virus, Dengue virus, West Nile virus, Respiratory Syncytial virus, Hepatitis C virus, thereby modulating innate immune signaling in the vertebrate, wherein the at least one compound has the structure:

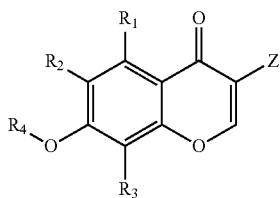

wherein $R_1$, $R_2$ and $R_3$ (independently) are H, lower alkyl, or OH, $R_4$ is alkylsulfonyl, and Z is aryl substituted with at least one group including Cl, $NO_2$, $CF_3$, alkylcarbonyl, or alkylsulfonyl, and optionally at least one additional group including H, lower alkyl, Br, Cl, F, OH, $NH_2$, $NO_2$, $OCF_3$, $CF_3$, alkylcarbonyl, or alkylsulfonyl.

2. The method of claim 1, wherein at least one additional anti-viral pharmaceutical agent is provided to the vertebrate.

3. The method of claim 2, wherein the at least one additional anti-viral pharmaceutical agent is provided in a pharmaceutical composition with the at least one compound or in a pharmaceutical composition without the at least one compound.

4. The method of claim 2, wherein the at least one additional anti-viral pharmaceutical agent is at least one of PEGinterferon α-2a, PEGinterferon α-2b, Ribavirin, Oseltamivir, Zanamivir, Amantadine, or Rimantadine.

5. The method of claim 1, wherein the selected threshold of step (d) is four standard deviations above control level.

6. The method of claim 1, wherein, prior to step (a), the putative RIG-I pathway modulating compounds are selected for predicted binding to the ligand-binding domain of RIG-I.

7. The method of claim 1, wherein the cells are U2OS cells, PH5CH8 cells, HeLa cells, Hep2 cells, MRC5 cells, A549 cells, or Huh 7 cells.

8. The method of claim 1, wherein the one or more viral countermeasures is at least one of NS3/4a, 3ABC, V protein, NS1, NS2, or VP35.

9. The method of claim 1, wherein the vertebrate is a human, a bird, a dog, a cat, or a farm animal.

10. The method of claim 1, wherein the reporter gene is luciferase.

11. The method of claim 1, wherein the at least one compound modulates the RIG-I pathway by activating interferon regulatory factor-3 (IRF-3).

* * * * *

UNITED STATES PATENT AND TRADEMARK OFFICE
CERTIFICATE OF CORRECTION

PATENT NO. : 9,458,492 B2  
APPLICATION NO. : 14/001472  
DATED : October 4, 2016  
INVENTOR(S) : S. P. Iadonato et al.

Page 1 of 1

It is certified that error appears in the above-identified patent and that said Letters Patent is hereby corrected as shown below:

On the Title Page

| Column | Line | Error |
|---|---|---|
| (75), Column 1 | Inventors | "Shawn P Iadonato," should read -- Shawn P. Iadonato, -- |

Signed and Sealed this  
Twelfth Day of June, 2018

Andrei Iancu  
*Director of the United States Patent and Trademark Office*